(12) United States Patent
Senaratne et al.

(10) Patent No.: US 10,494,651 B2
(45) Date of Patent: Dec. 3, 2019

(54) CONTROL OF CONDUCTIVITY IN ANAEROBIC FERMENTATION

(71) Applicants: Ryan H. Senaratne, Fayetteville, AR (US); Peter Simpson Bell, Dunblane (GB); Song Liu, Fayetteville, AR (US); Syrona R. Scott, Fayetteville, AR (US)

(72) Inventors: Ryan H. Senaratne, Fayetteville, AR (US); Peter Simpson Bell, Dunblane (GB); Song Liu, Fayetteville, AR (US); Syrona R. Scott, Fayetteville, AR (US)

(*) Notice: Subject to any disclaimer, the term of this patent is extended or adjusted under 35 U.S.C. 154(b) by 0 days.

(21) Appl. No.: 15/811,933

(22) Filed: Nov. 14, 2017

(65) Prior Publication Data

US 2019/0225995 A1 Jul. 25, 2019

Related U.S. Application Data

(62) Division of application No. 14/293,089, filed on Jun. 2, 2014, now Pat. No. 9,850,503.

(60) Provisional application No. 61/833,189, filed on Jun. 10, 2013.

(51) Int. Cl.
*C12P 7/06* (2006.01)
*C12N 1/20* (2006.01)
*C12M 1/34* (2006.01)

(52) U.S. Cl.
CPC ............. *C12P 7/065* (2013.01); *C12M 41/00* (2013.01); *C12N 1/20* (2013.01); *Y02E 50/17* (2013.01)

(58) Field of Classification Search
CPC .......... C12M 41/00; C12N 1/20; C12P 7/065; Y02E 50/17
See application file for complete search history.

(56) References Cited

U.S. PATENT DOCUMENTS

2014/0080169 A1* 3/2014 Senaratne .............. G01N 21/31
435/29

OTHER PUBLICATIONS

Younesi et al. Biochem. Engineer. J. (2005) 27:110-119 (Year: 2005).*

* cited by examiner

*Primary Examiner* — Susan M Hanley
(74) *Attorney, Agent, or Firm* — James P. Krueger

(57) ABSTRACT

Process are provided which are effective for controlling medium conductivity during fermentation of a CO-containing gaseous substrate while providing an STY of about 10 g ethanol/(L·day) or more. The process includes balancing medium conductivity, specific carbon uptake or cell density levels.

6 Claims, 26 Drawing Sheets

CONTROL OF CONDUCTIVITY IN ANAEROBIC FERMENTATION

This application is a divisional of U.S. application Ser. No. 14/293,089 filed Jun. 2, 2014 now U.S. Pat. No. 9,850,503, which claims the benefit of U.S. Provisional Application No. 61/833,189 which was filed on Jun. 10, 2013, and which is incorporated in its entirety herein by reference.

A process is provided for controlling conductivity during syngas fermentation and maintaining an STY of about 10 g ethanol/(L·day) or more. More specifically, processes for controlling conductivity include balancing medium conductivity, specific carbon uptake, or cell density.

BACKGROUND

Anaerobic microorganisms can produce ethanol from CO through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic acetogenic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

Acetogenic bacteria require a constant feed of nutrients for stable performance and ethanol productivity. Higher productivity levels may require the use of more concentrated mediums to provide effective amounts of nutrients. Use of more concentrated mediums results in a fermentation broth with a higher ionic strength. Higher ionic strength causes detrimental effects on culture performance.

SUMMARY

Process are provided which are effective for controlling medium conductivity during fermentation of a CO-containing gaseous substrate while providing an STY of about 10 g ethanol/(L·day) or more. The process includes balancing medium conductivity, specific carbon uptake or cell density levels.

A process for fermenting a CO-containing gaseous substrate includes providing a CO-containing gaseous substrate to a fermentation medium. In one aspect, the process includes maintaining a conductivity to specific carbon uptake (SCU in mmole/minute/gram dry cells) relationship according to a formula where $SCU=SCU_{max}-F*conductivity$, wherein $SCU_{max}=0$ to 3 and $F=0$ to 1. The fermentation medium has a conductivity of about 30 mS/cm or less and the process is effective for maintaining an STY of about 10 g ethanol/(L·day) or more.

A process for fermenting a CO-containing gaseous substrate includes providing a CO-containing gaseous substrate to a fermentation medium and fermenting the syngas. The process further includes maintaining a conductivity (y) to specific gas feed rate (x) according to a formula where $y=-6.0327x+12.901$, until reaching a target cell density, wherein x is about 0.2 to about 0.7 mmole/minute/gram of cells. In another aspect, the process includes maintaining a cell density above a target cell density and maintaining a conductivity of about 30 mS/cm or less. The process is effective for maintaining an STY of about 10 g ethanol/(L·day) or more.

A process for fermentation of a CO-containing gaseous substrate includes introducing the CO-containing gaseous substrate into a reactor vessel that includes a fermentation medium and fermenting the CO-containing gaseous substrate. In one aspect of the process, at least one or more chloride ions in the fermentation medium are substituted with an ion selected from the group consisting of hydroxide, acetate, carbonate, bicarbonate and mixtures thereof in an amount effective for providing a conductivity of about 30 mS/cm or less. The process is effective for maintaining an STY of about 10 g ethanol/(L·day) or more.

BRIEF DESCRIPTION OF FIGURES

The above and other aspects, features and advantages of several aspects of the process will be more apparent from the following figures.

Figure 25:
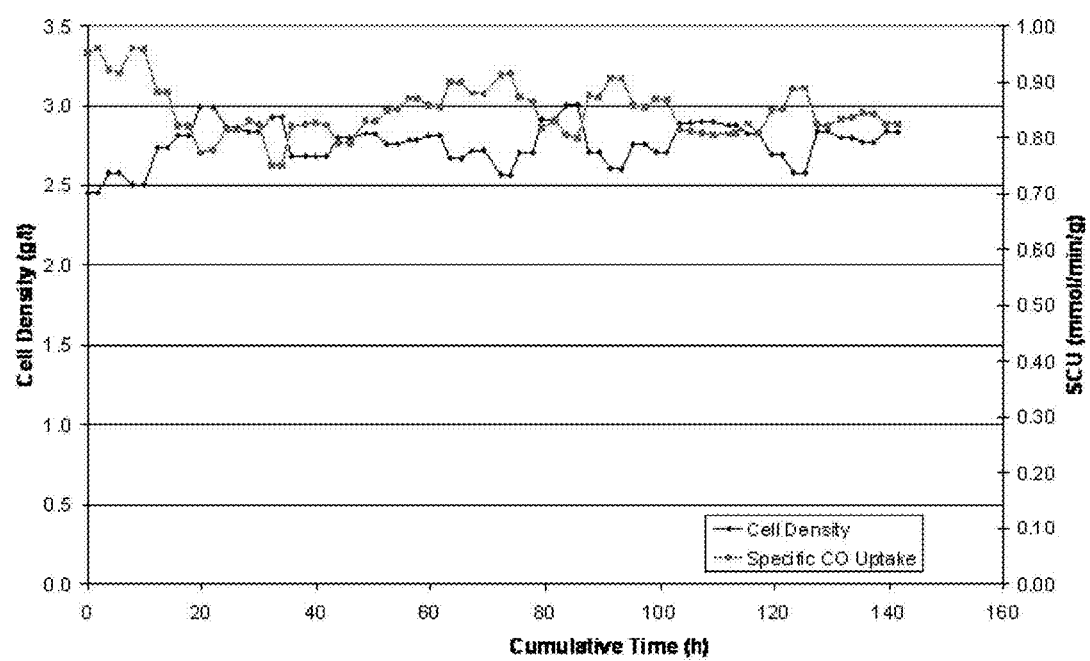

Specific carbon uptake of *Clostridium ljungdahlii* growing in medium with ammonium bicarbonate is shown in FIG. 25.

Figure 26:
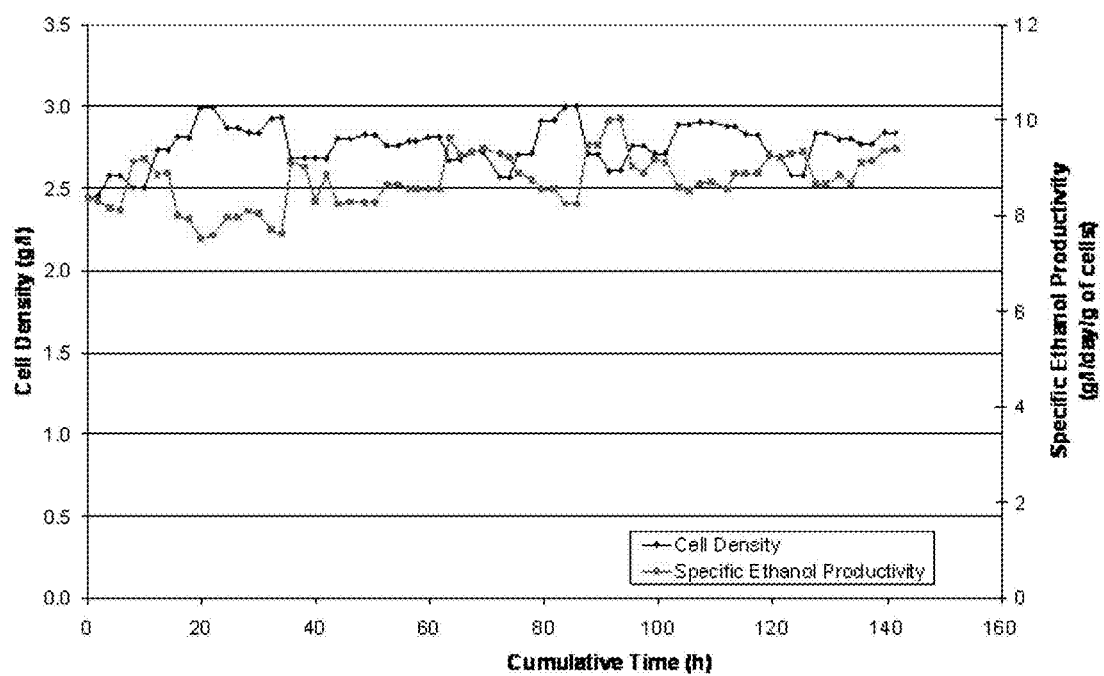

Specific ethanol productivity of *Clostridium ljungdahlii* growing in medium with ammonium bicarbonate is shown in FIG. 26.

Figure 27:
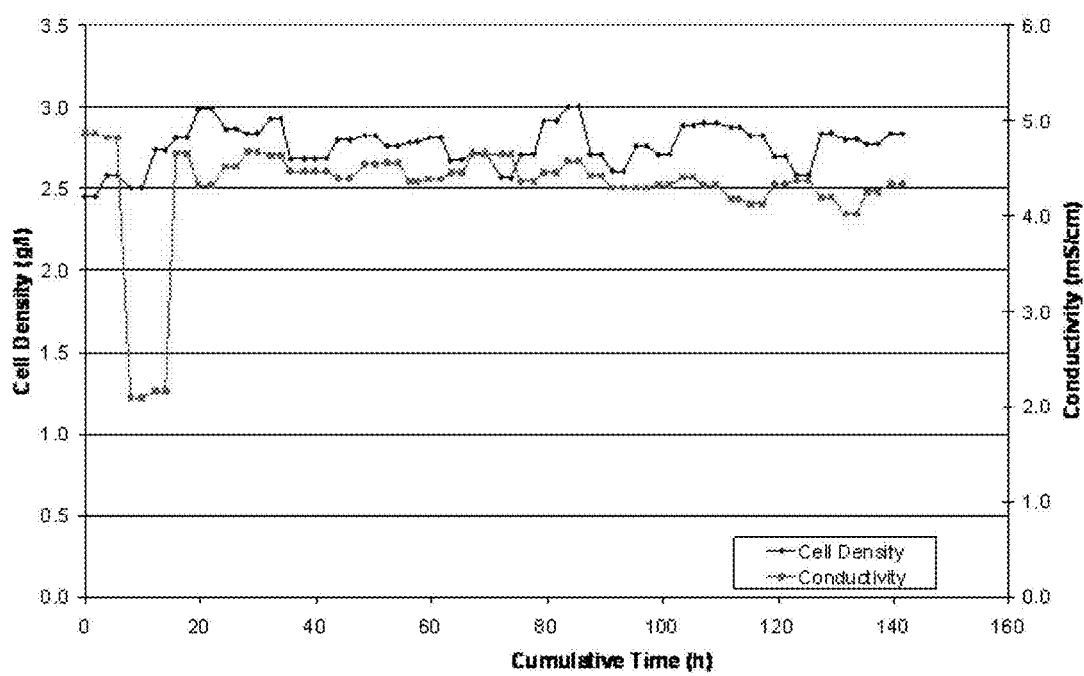

Conductivity of *Clostridium ljungdahlii* growing in medium with ammonium bicarbonate is shown in FIG. 27.

Figure 28:
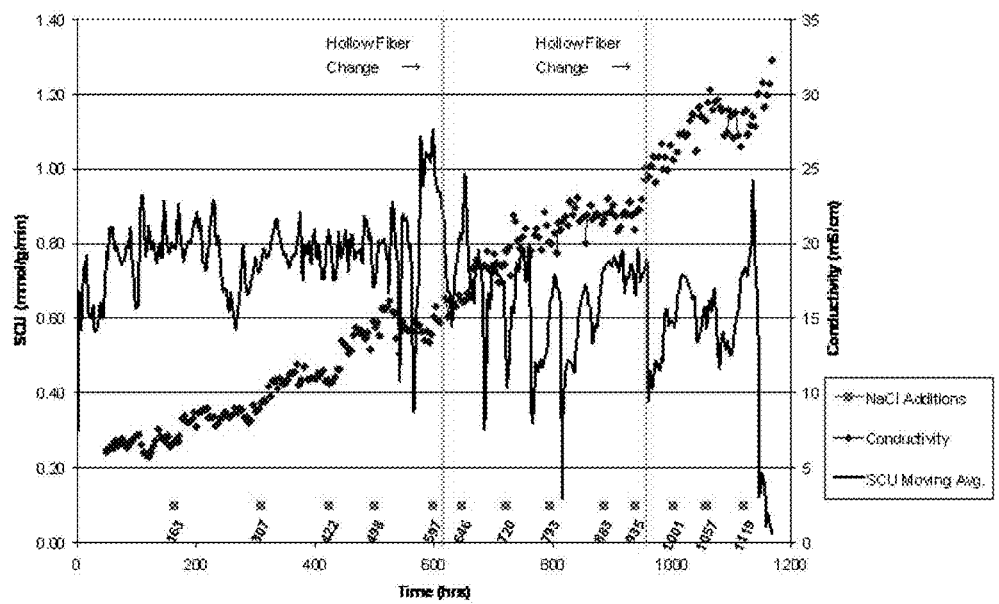

FIG. 28 illustrates effects of step-wise increases in medium conductivity on performance of *Clostridium ljungdahlii*.

Figure 29:
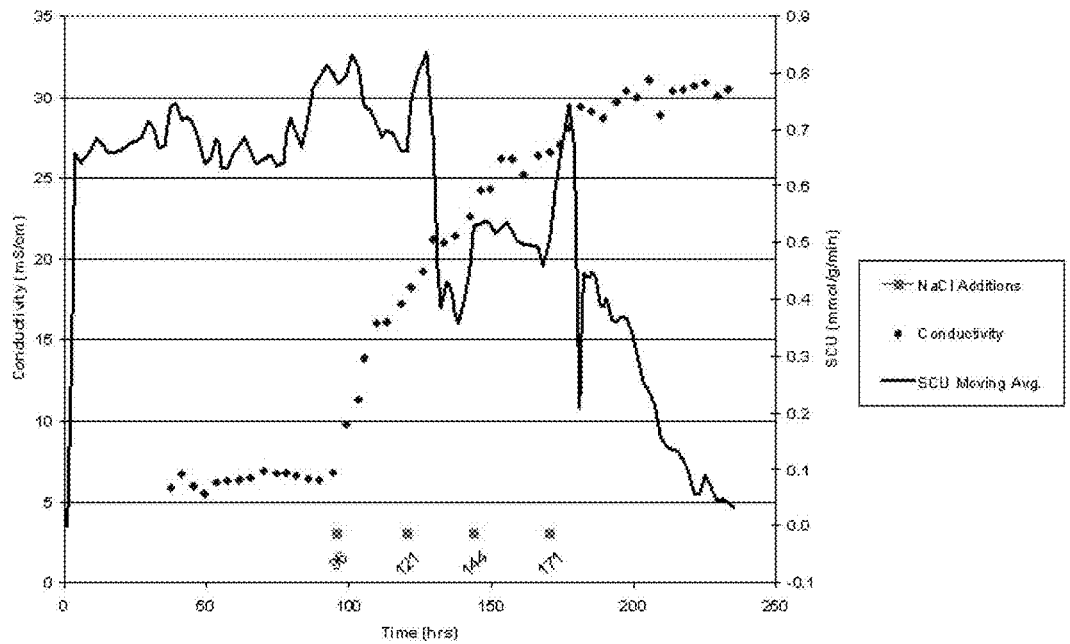

FIG. 29 illustrates effects of step-wise increases in medium conductivity on performance of *Clostridium ljungdahlii*.

Figure 30:
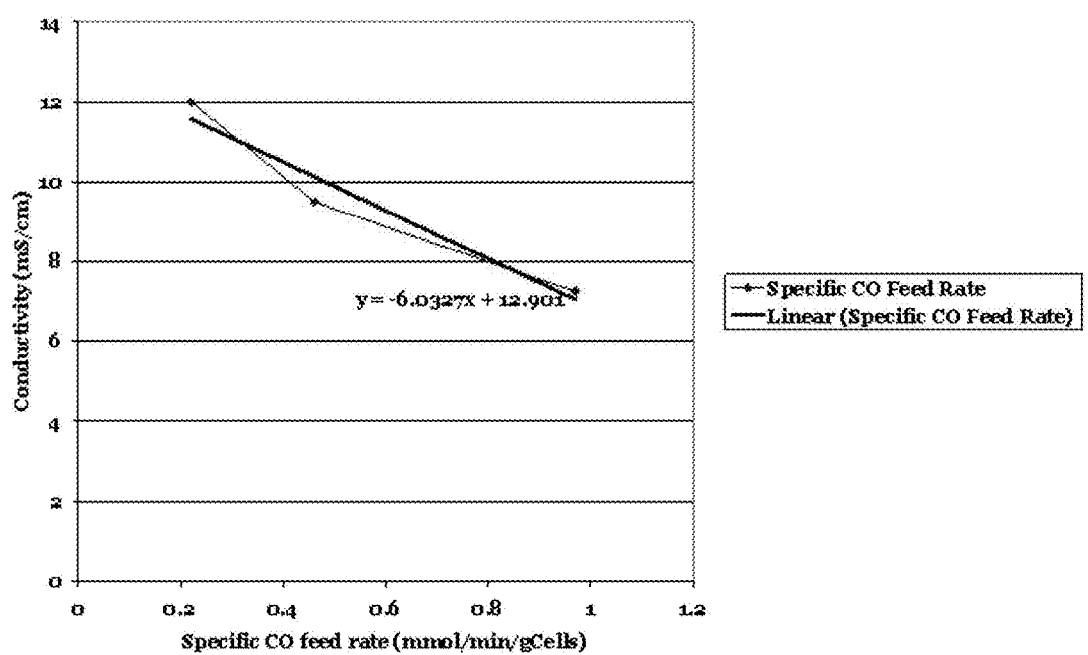

FIG. 30 shows the relationship between specific CO feed rate and conductivity during fermentation of *Clostridium ljungdahlii*.

Figure 31:
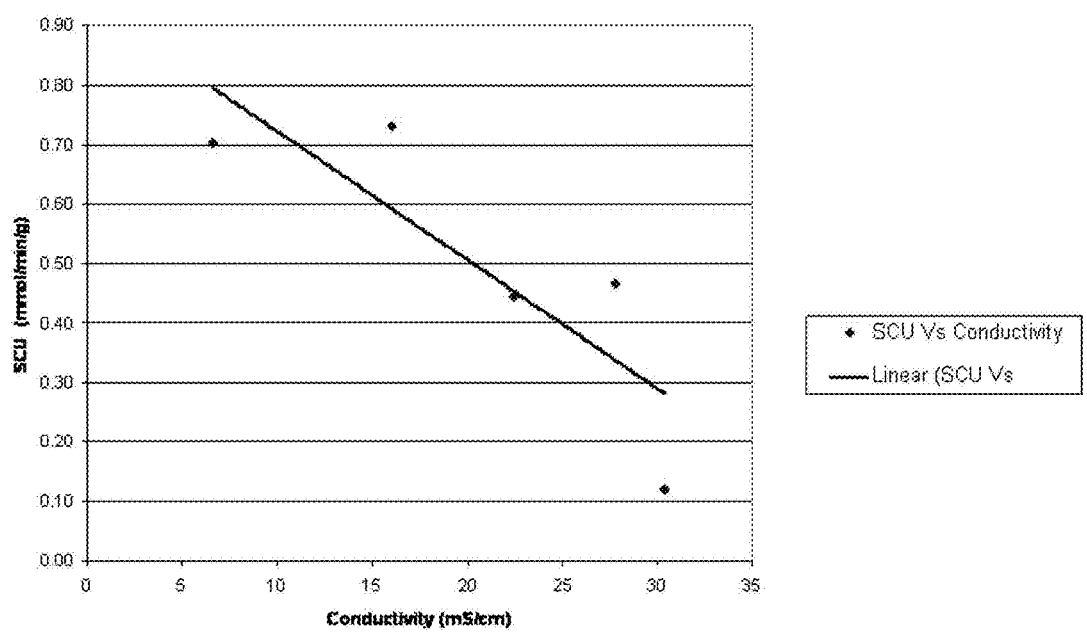

FIG. 31 shows the relationship between specific carbon uptake and conductivity during fermentation of *Clostridium ljungdahlii*.

Corresponding reference characters indicate corresponding components throughout the several views of the figures. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects of the present process and apparatus. Also, common but well-understood elements that are useful or necessary in commercially feasible aspects are often not depicted in order to facilitate a less obstructed view of these various aspects.

DETAILED DESCRIPTION

The following description is not to be taken in a limiting sense, but is made merely for the purpose of describing the general principles of exemplary embodiments. The scope of the invention should be determined with reference to the claims.

Syngas fermentations conducted in bioreactors with medium and acetogenic bacteria as described herein are effective for providing conversions of CO in syngas into alcohols and other products. Control of conductivity, conductivity, and cell density is effective for providing high productivity levels. In this aspect, alcohol productivity may be expressed as STY (space time yield expressed as g ethanol/(L·day). In this aspect, the process is effective for providing a STY (space time yield) of at least about 10 g ethanol/(L·day). Possible STY values include about 10 g ethanol/(L·day) to about 200 g ethanol/(L·day), in another aspect, about 10 g ethanol/(L·day) to about 160 g ethanol/(L·day), in another aspect, about 10 g ethanol/(L·day) to about 120 g ethanol/(L·day), in another aspect, about 10 g ethanol/(L·day) to about 80 g ethanol/(L·day), in another aspect, about 20 g ethanol/(L·day) to about 140 g ethanol/(L·day), in another aspect, about 20 g ethanol/(L·day) to about 100 g ethanol/(L·day), in another aspect, about 40 g ethanol/(L·day) to about 140 g ethanol/(L·day), and in another aspect, about 40 g ethanol/(L·day) to about 100 g ethanol/(L·day).

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

"Conductivity" and "average conductivity" refer to the ability to conduct electricity. Water conducts electricity because it contains dissolved solids that carry electrical charges. For example, chloride, nitrate, and sulfate carry negative charges, while sodium, magnesium, and calcium carry positive charges. These dissolved solids affect the water's ability to conduct electricity. Conductivity is measured by a probe, which applies voltage between two electrodes. The drop in voltage is used to measure the resistance of the water, which is then converted to conductivity. Average conductivity may be measured by known techniques and methods. Some examples of average conductivity measurements are provided in ASTM D1125, "Standard Test Methods for Electrical Conductivity and Resistivity of Water", and in "Standard Methods for the Examination of Water and Wastewater", 1999, American Public Health Association, American Water Works Association, Water Environment Federation, both of which are incorporated herein by reference.

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The terms "fermentation", "fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation broth, for example, grams/liter. In this aspect, the process and mediums are effective for providing a cell density of at least about 1.0 g/L.

The term "cell recycle" refers to separation of microbial cells from a fermentation broth and returning all or part of those separated microbial cells back to the fermentor. Generally, a filtration device is used to accomplish separations.

The term "fermentor", "reactor vessel" or "bioreactor", includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

CO-Containing Substrate

A CO-containing substrate may include any gas that includes CO. In this aspect, a CO-containing gas may include syngas, industrial gases, and mixtures thereof.

Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. Some examples of suitable gasification methods and apparatus are provided in U.S. Ser. Nos. 61/516,667, 61/516,704 and 61/516,646, all of which were filed on Apr. 6, 2011, and in U.S. Ser. Nos. 13/427,144, 13/427,193 and 13/427,247, all of which were filed on Mar. 22, 2012, and all of which are incorporated herein by reference.

In another aspect, the process has applicability to supporting the production of alcohol from gaseous substrates such as high volume CO-containing industrial flue gases. In some aspects, a gas that includes CO is derived from carbon containing waste, for example, industrial waste gases or from the gasification of other wastes. As such, the processes represent effective processes for capturing carbon that would otherwise be exhausted into the environment. Examples of industrial flue gases include gases produced during ferrous metal products manufacturing, non-ferrous products manufacturing, petroleum refining processes, gasification of coal, gasification of biomass, electric power production, carbon black production, ammonia production, methanol production and coke manufacturing.

Depending on the composition of the CO-containing substrate, the CO-containing substrate may be provided directly to a fermentation process or may be further modified to include an appropriate $H_2$ to CO molar ratio. In one aspect, CO-containing substrate provided to the fermentor has an $H_2$ to CO molar ratio of about 0.2 or more, in another aspect, about 0.25 or more, and in another aspect, about 0.5 or more. In another aspect, CO-containing substrate provided to the fermentor may include about 40 mole percent or more CO plus $H_2$ and about 30 mole percent or less CO, in another aspect, about 50 mole percent or more CO plus $H_2$ and about 35 mole percent or less CO, and in another aspect, about 80 mole percent or more CO plus $H_2$ and about 20 mole percent or less CO.

In one aspect, the CO-containing substrate mainly includes CO and $H_2$. In this aspect, the CO-containing substrate will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. The CO-containing substrate will have a $CO/CO_2$ ratio of at least about 0.75, in another aspect, at least about 1.0, and in another aspect, at least about 1.5.

In one aspect, a gas separator is configured to substantially separate at least one portion of the gas stream, wherein the portion includes one or more components. For example, the gas separator may separate $CO_2$ from a gas stream comprising the following components: CO, $CO_2$, $H_2$, wherein the $CO_2$ may be passed to a $CO_2$ remover and the remainder of the gas stream (comprising CO and $H_2$) may be passed to a bioreactor. Any gas separator known in the art may be utilized. In this aspect, syngas provided to the fermentor will have about 10 mole % or less $CO_2$, in another aspect, about 1 mole % or less $CO_2$, and in another aspect, about 0.1 mole % or less $CO_2$.

Certain gas streams may include a high concentration of CO and low concentrations of $H_2$. In one aspect, it may be desirable to optimize the composition of the substrate stream in order to achieve higher efficiency of alcohol production and/or overall carbon capture. For example, the concentration of $H_2$ in the substrate stream may be increased before the stream is passed to the bioreactor.

According to particular aspects of the invention, streams from two or more sources can be combined and/or blended to produce a desirable and/or optimized substrate stream. For example, a stream comprising a high concentration of CO, such as the exhaust from a steel mill converter, can be combined with a stream comprising high concentrations of $H_2$, such as the off-gas from a steel mill coke oven.

Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Bioreactor Design and Operation

Descriptions of fermentor designs are described in U.S. Ser. Nos. 13/471,827 and 13/471,858, both filed May 15, 2012, and U.S. Ser. No. 13/473,167, filed May 16, 2012, all of which are incorporated herein by reference.

In accordance with one aspect, the fermentation process is started by addition of medium to the reactor vessel. Some examples of medium compositions are described in U.S. Ser. Nos. 61/650,098 and 61/650,093, filed May 22, 2012, and in U.S. Pat. No. 7,285,402, filed Jul. 23, 2001, all of which are incorporated herein by reference. The medium may be sterilized to remove undesirable microorganisms and the reactor is inoculated with the desired microorganisms. Sterilization may not always be required.

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi*

(CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The methods of the invention can be used to sustain the viability of a microbial culture, wherein the microbial culture is limited in CO, such that the rate of transfer of CO into solution is less than the uptake rate of the culture. Such situations may arise when a substrate comprising CO is not continuously provided to the microbial culture; the mass transfer rate is low; or there is insufficient CO in a substrate stream to sustain culture vitality at optimum temperature. In such embodiments, the microbial culture will rapidly deplete the CO dissolved in the liquid nutrient medium and become substrate limited as further substrate cannot be provided fast enough.

Startup:

Upon inoculation, an initial feed gas supply rate is established effective for supplying the initial population of microorganisms. Effluent gas is analyzed to determine the content of the effluent gas. Results of gas analysis are used to control feed gas rates. In this aspect, the process may provide a calculated CO concentration to initial cell density ratio of about 0.5 to about 0.9, in another aspect, about 0.6 to about 0.8, in another aspect, about 0.5 to about 0.7, and in another aspect, about 0.5 to about 0.6.

In another aspect, a fermentation process includes providing syngas to a fermentation medium in an amount effective for providing an initial calculated CO concentration in the fermentation medium of about 0.15 mM to about 0.70 mM, in another aspect, about 0.15 mM to about 0.50 mM, in another aspect, about 0.15 mM to about 0.35 mM, in another aspect, about 0.20 mM to about 0.30 mM, and in another aspect, about 0.23 mM to about 0.27 mM. The process is effective for increasing cell density as compared to a starting cell density.

In one aspect, a process for fermenting a CO-containing gaseous substrate includes providing a CO-containing gaseous substrate to a fermentation medium and maintaining a conductivity to specific carbon uptake (SCU in mmole/minute/gram dry cells) according to a formula where $SCU = SCU_{max} - F*conductivity$, wherein $SCU_{max} = 0$ to 3 and $F = 0$ to 1. FIG. 31 graphically illustrates this equation. In this aspect, the fermentation medium has a conductivity of about 30 mS/cm or less and in other aspects, may have the conductivity as describe herein. In another aspect, F (which is the slope of the line) may be 0 to 1, in another aspect, 0.05 to 1, in another aspect, 0.1 to 1, in another aspect, 0.2 to 1, in another aspect, 0.3 to 1, in another aspect, 0.4 to 1, and in another aspect, 0.5 to 1.

In one aspect, the process includes maintaining a conductivity (y) to specific gas feed rate (x) according to a formula $y = -10.109x + 14.2$ until reaching a target cell density. FIG. 30 graphically illustrates this equation. In this aspect, the fermentation medium has a conductivity of about 30 mS/cm or less and in other aspects, may have the conductivity as describe herein. In this aspect, x is about 0.2 to about 0.7 mmole/minute/gram of cells. In another aspect, x is about 0.3 to about 0.6 mmole/minute/gram of cells, and in another aspect, x is about 0.4 to about 0.5 mmole/minute/gram of cells.

In another aspect, the process is effective for providing a target cell density of about 3 to about 30 g/L, in another aspect, about 4 to about 25 g/L, in another aspect, about 5 to about 25 g/L, in another aspect, about 7 to about 25 g/L, in another aspect, about 10 to about 25 g/L, in another aspect, about 12 to about 20 g/L, and in another aspect, about 15 to about 20 g/L.

Post-Startup:

Upon reaching desired levels, liquid phase and cellular material is withdrawn from the reactor and replenished with medium. The process is effective for increasing cell density to about 2.0 grams/liter or more, in another aspect, about 2 to about 30 grams/liter, in another aspect, about 2 to about 25 grams/liter, in another aspect, about 2 to about 20 grams/liter, in another aspect, about 2 to about 10 grams/liter, in another aspect, about 2 to about 8 grams/liter, in another aspect, about 3 to about 30 grams/liter, in another aspect, about 3 to about 6 grams/liter, and in another aspect, about 4 to about 5 grams/liter.

Upon reaching a target cell density, the process is effective for maintaining a cell density. Cell density may be maintained through cell recycle. The process may utilize cell recycle to increase or decrease cell concentration inside the reactor. In this aspect, liquid effluent from the reactor is sent to a cell separator where cells and permeate are separated. Cells may be sent back to the reactor. Cell density may be controlled through a recycle filter. Some examples of bioreactors and cell recycle are described U.S. Ser. Nos. 61/571, 654 and 61/571,565, filed Jun. 30, 2011, U.S. Ser. No. 61/573,845, filed Sep. 13, 2011, U.S. Ser. Nos. 13/471,827 and 13/471,858, filed May 15, 2012, and U.S. Ser. No. 13/473,167, filed May 16, 2012, all of which are incorporated herein by reference.

In one aspect, the process is effective for maintaining an $H_2$ conversion of about 25% or more. In another aspect, the process is effective for maintaining an $H_2$ conversion of about 25% to about 95%, in another aspect, about 30% to about 90%, in another aspect, about 35% to about 85%, in another aspect, about 40% to about 80%, in another aspect, about 40% to about 70%, in another aspect, about 40% to about 60%, and in another aspect, about 40% to about 50%.

In another aspect, the process is effective for maintaining a CO uptake in a range of about 0.001 to about 10 mmole/minute/gram of dry cells. In another aspect, the process is effective for maintaining CO uptake in a range of about 0.001 to about 5 mmole/minute/gram of dry cells, in another aspect, about 0.001 to about 4 mmole/minute/gram of dry cells, in another aspect, about 0.001 to about 3 mmole/minute/gram of dry cells, in another aspect, about 0.001 to about 2 mmole/minute/gram of dry cells, in another aspect, about 0.001 to about 1 mmole/minute/gram of dry cells, in another aspect, about 0.05 to about 9 mmole/minute/gram of dry cells, in another aspect, about 0.05 to about 5 mmole/minute/gram of dry cells, in another aspect, about 0.05 to about 4 mmole/minute/gram of dry cells, in another aspect, about 0.05 to about 3 mmole/minute/gram of dry cells, in another aspect, about 0.05 to about 2 mmole/minute/gram of dry cells, in another aspect, about 0.05 to about 1 mmole/minute/gram of dry cells, in another aspect, about 1 to about 8 mmole/minute/gram of dry cells, in another aspect, about 1 to about 5 mmole/minute/gram of dry cells, in another aspect, about 1 to about 4 mmole/minute/gram of dry cells, in another aspect, about 1 to about 3 mmole/minute/gram of dry cells, and in another aspect, about 1 to about 2 mmole/minute/gram of dry cells.

In one aspect, the process is effective for providing a CO conversion of about 5 to about 99%. In another aspect, CO conversion is about 10 to about 90%, in another aspect, about 20 to about 80%, in another aspect, about 30 to about 70%, in another aspect, about 40 to about 60%, in another aspect, about 50 to about 95%, in another aspect, about 60 to about 95%, in another aspect, about 70 to about 95%, and in another aspect, about 80 to about 95%.

Control of Medium Conductivity

Use of mediums formulated to have lower conductivity and/or adjustment of medium conductivity by dilution are effective for controlling medium conductivity. In one aspect, the process is effective for providing an average conductivity of about 30 mS/cm or less, in another aspect, about 25 mS/cm or less, in another aspect, about 20 mS/cm or less, in another aspect, 16 mS/cm or less, in another aspect, about 12 mS/cm or less, in another aspect, about 8 mS/cm or less, in another aspect, about 6.5 mS/cm or less, in another aspect, about 6.0 mS/cm or less, in another aspect, about 5.5 mS/cm or less, in another aspect, about 5.0 mS/cm or less, in another aspect, about 4.7 mS/cm or less, in another aspect, about 4.5 mS/cm or less, in another aspect, about 4.0 mS/cm to about 6.5 mS/cm, in another aspect, about 5.0 mS/cm to about 6.0 mS/cm, and in another aspect, about 4.0 mS/cm to about 5.0 mS/cm.

In accordance with one aspect, the fermentation process is started by addition of a suitable medium to the reactor vessel. The liquid contained in the reactor vessel may include any type of suitable nutrient medium or fermentation medium. The nutrient medium will include vitamins and minerals effective for permitting growth of the microorganism being used. Anaerobic medium suitable for the fermentation of ethanol using CO as a carbon source are known. One example of a suitable fermentation medium is described in U.S. Pat. No. 7,285,402, which is incorporated herein by reference. Other examples of suitable medium are described in U.S. Ser. Nos. 61/650,098 and 61/650,093, both filed on May 22, 2012, and which are both incorporated herein by reference. In one aspect, the medium utilized includes less than about 0.01 g/L yeast extract and less than about 0.01 g/L carbohydrates.

Substitution of Chloride Ion:

In one aspect, the process provides mediums having an average conductivity of less than about 30 mS/cm by substituting chloride ions in the medium with a non-chloride ion. More specifically, ammonium chloride may be substituted with a nitrogen source selected from the group consisting of ammonium hydroxide, ammonium acetate, ammonium carbonate, ammonium bicarbonate and mixtures thereof.

In one aspect, the medium includes at least one or more of a nitrogen source, at least one or more phosphorous source and at least one or more of a potassium source. The medium may include any one of the three, any combination of the three, and in an important aspect, includes all three. A phosphorous source may include a phosphorous source selected from the group consisting of phosphoric acid, ammonium phosphate, potassium phosphate, and mixtures thereof. A potassium source may include a potassium source selected from the group consisting of potassium chloride, potassium phosphate, potassium nitrate, potassium sulfate, and mixtures thereof.

In one aspect, the medium includes one or more of iron, tungsten, nickel, cobalt, magnesium, sulfur and thiamine. The medium may include any one of these components, any combination, and in an important aspect, includes all of these components. An iron may include an iron source selected from the group consisting of ferrous chloride, ferrous sulfate, and mixtures thereof. A tungsten source may include a tungsten source selected from the group consisting of sodium tungstate, calcium tungstate, potassium tungstate, and mixtures thereof. A nickel source may include a nickel source selected from the group consisting of nickel chloride, nickel sulfate, nickel nitrate, and mixtures thereof. A cobalt source may include a cobalt source selected from the group consisting of cobalt chloride, cobalt fluoride, cobalt bromide, cobalt iodide and mixtures thereof. A magnesium source may include a magnesium source selected from the group consisting of magnesium chloride, magnesium sulfate, magnesium phosphate, and mixtures thereof. A sulfur source may include cysteine, sodium sulfide, and mixtures thereof.

Concentrations of various components are as follows:

| Component | Concentration Range (expressed as mg or µg nutrient per gram of cells) | Preferred Range (expressed as mg or µg nutrient per gram of cells) |
| --- | --- | --- |
| nitrogen (N) | 100-340 mg | 190-210 mg |
| phosphorus (P) | 10.5-15 mg | 12-13 mg |
| potassium (K) | 26-36 mg | 28-33 mg |
| iron (Fe) | 2.7-5 mg | 3.0-4.0 mg |
| tungsten (W) | 10-30 µg | 15-25 µg |
| Nickel (Ni) | 34-40 µg | 35-37 µg |
| Cobalt (Co) | 9-30 µg | 15-20 µg |
| Magnesium (Mg) | 4.5-10 mg | 5-7 mg |

-continued

| Component | Concentration Range (expressed as mg or µg nutrient per gram of cells) | Preferred Range (expressed as mg or µg nutrient per gram of cells) |
|---|---|---|
| Sulfur (S) | 11-20 mg | 12-16 mg |
| Thiamine | 6.5-20 µg | 7-12 µg |

Process operation maintains a pH in a range of about 4.2 to about 4.8. The medium includes less than about 0.01 g/L yeast extract and less than about 0.01 g/L carbohydrates.

In another aspect, the process control medium conductivity through dilution of medium. In this aspect, once the fermentation reaches a conductivity of about 30 mS/cm, the process includes addition of water or a low conductivity medium to the fermentation in an amount effective to lower the medium conductivity.

EXAMPLES

Example 1: Effect of Conductivity on Growth

*Clostridium ljungdahlii* was grown in a bioreactor (New Brunswick BioFlo I or IIc). The following adjustments were made:

Conductivity of the culture was adjusted by adjusting the strength of the growth medium, for example concentration of all the components, except vitamin in the growth medium was increased by 1.5 times to increase the conductivity of the culture from approximately 7 mS to approximately 9.5 mS.

All experiments were started with the initial cell density of 0.38 (+/−0.02) or 0.48 g/L.

Initial gas flow rate of each experiment was kept unchanged throughout the experiment. Reactor parameters, when CO conversion values reach a plateau after a successful start-up, were used to calculate $K_{La}$ for relevant conditions.

Syngas composition was 30% CO, 15% $H_2$, 10% $CO_2$ and 45% $N_2$.

Figure 1:
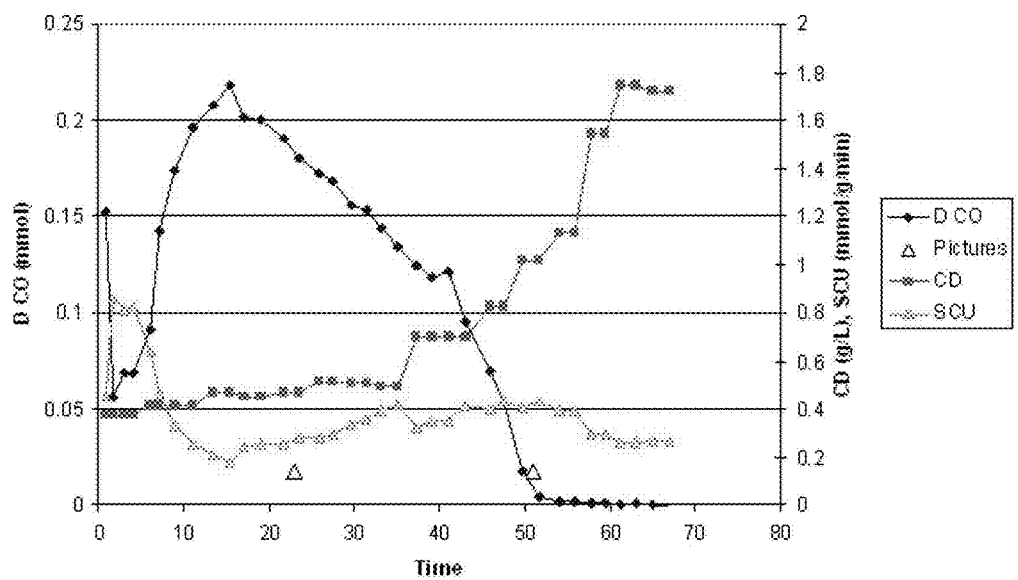
FIG. 1 illustrates growth of *Clostridium ljungdahlii* in 1× growth medium and a 25 ml/min syngas feed rate.

Bioreactor Run #1:

1× growth medium and 25 ml/min syngas feed rate was used in this experiment. As shown in FIG. 1, after an initial lag period of about 20 hours bacteria started to multiply at a doubling time of about 20 hours. Maximum calculated dissolved CO was about 0.22 mmol in the reactor broth. (D CO: dissolved CO concentration in the reactor broth, CD: cell density, SCU specific CO uptake.)

Figure 2:
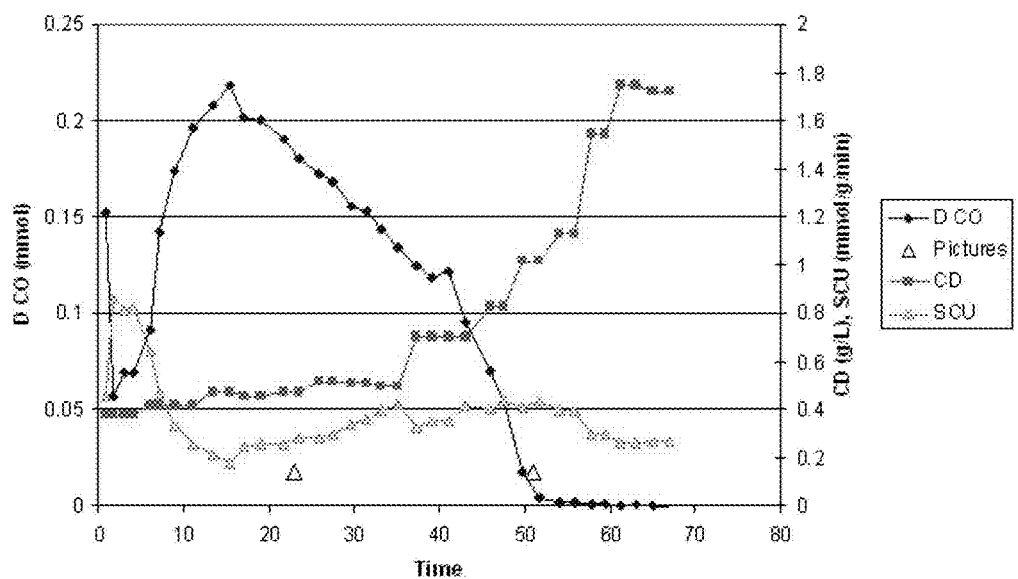
FIG. 2 illustrates growth of *Clostridium ljungdahlii* in 1× growth medium and a 35 ml/min syngas feed rate.

Bioreactor Run #2:

1× growth medium and 35 ml/min syngas feed rate was used in this experiment. As shown in FIG. 2, after initial lag period of about 36 hours bacteria started to multiply at a doubling time of about 20 hours. Maximum calculated dissolved CO was about 0.22 mmol in the reactor broth.

Figure 3:
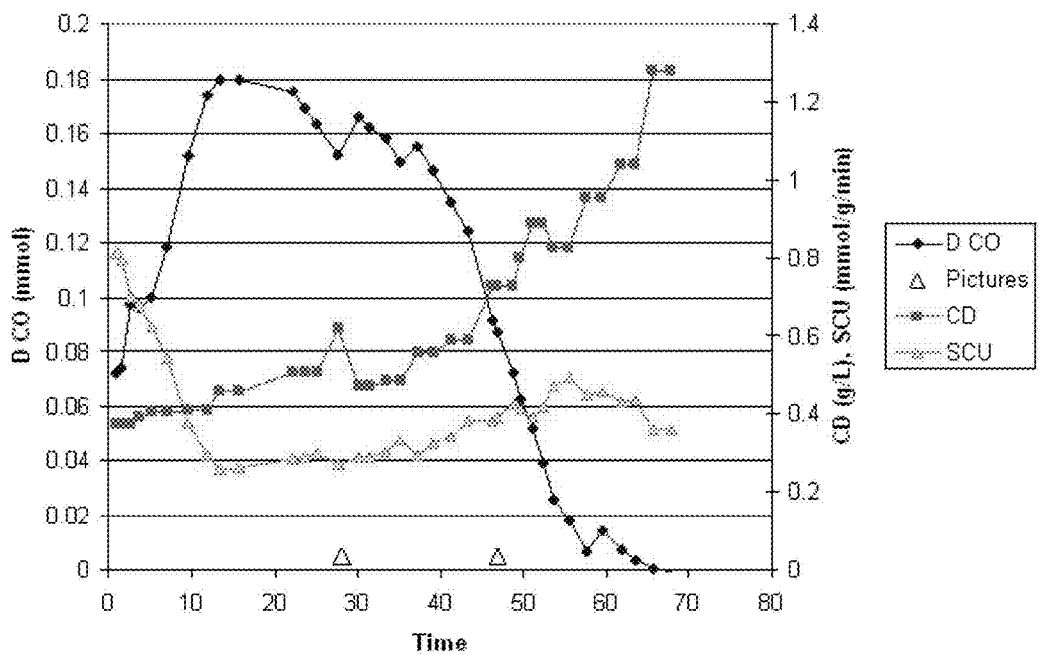
FIG. 3 illustrates growth of *Clostridium ljungdahlii* in 1× growth medium and a 40 ml/min syngas feed rate.

Bioreactor Run #3:

1× growth medium and 40 ml/min syngas feed rate was used in this experiment. As shown in the FIG. 3, after initial lag period of about 45 hours bacteria started to multiply at a doubling time of about 20 hours. Maximum calculated dissolved CO was about 0.22 mmol in the reactor broth.

Figure 4:
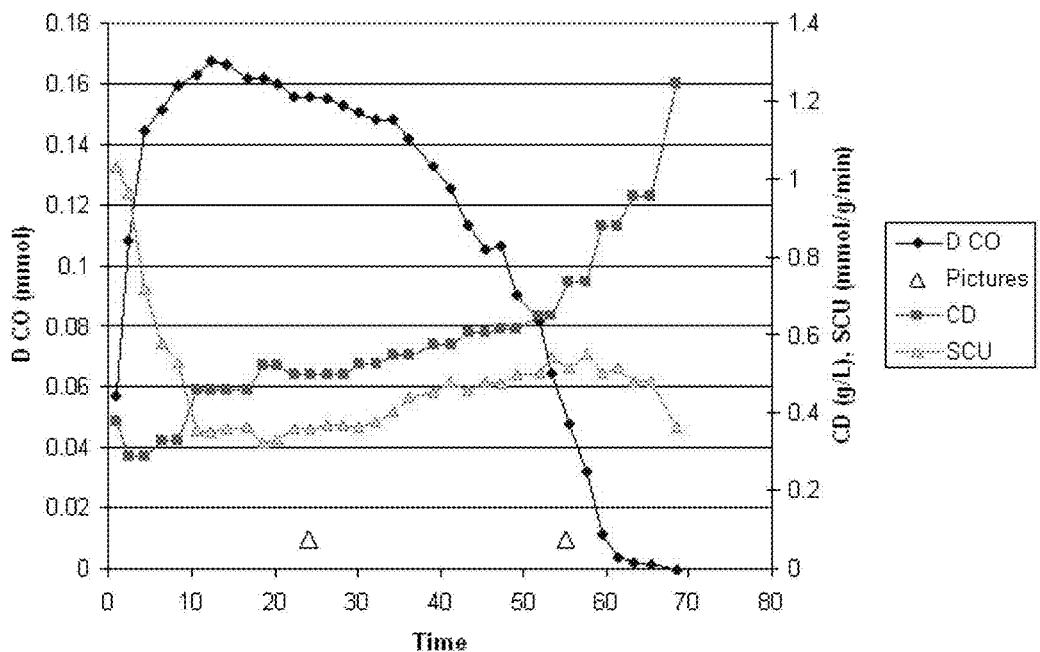
FIG. 4 illustrates growth of *Clostridium ljungdahlii* in 1× growth medium and a 45 ml/min syngas feed rate.

Bioreactor Run #4:

1× growth medium and 45 ml/min syngas feed rate was used in this experiment. As shown in the FIG. 4, after an initial lag period of about 50 hours, bacteria started to multiply at a doubling time of about 20 hours. Maximum calculated dissolved CO was around 0.17 mmol in the reactor broth.

Figure 5:
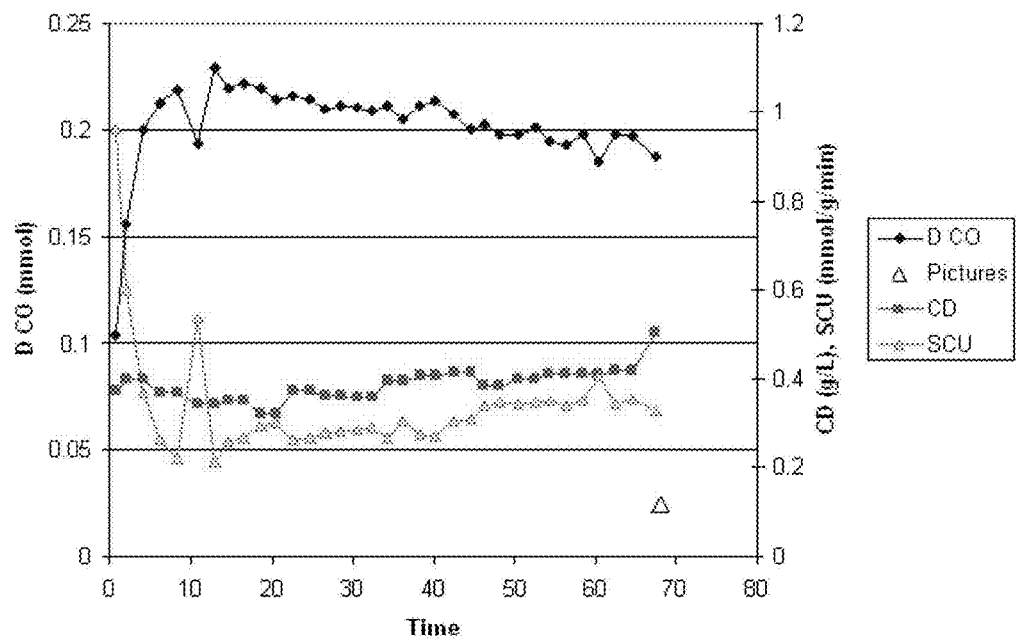
FIG. 5 illustrates growth of *Clostridium ljungdahlii* in 1× growth medium and a 50 ml/min syngas feed rate.

Bioreactor Run #5:

1× growth medium and 50 ml/min syngas feed rate was used in this experiment. As shown in FIG. 5, culture continued to lag even at about 70 hours after inoculation. Maximum calculated dissolved CO was about 0.23 mmol in the reactor broth.

Figure 6:
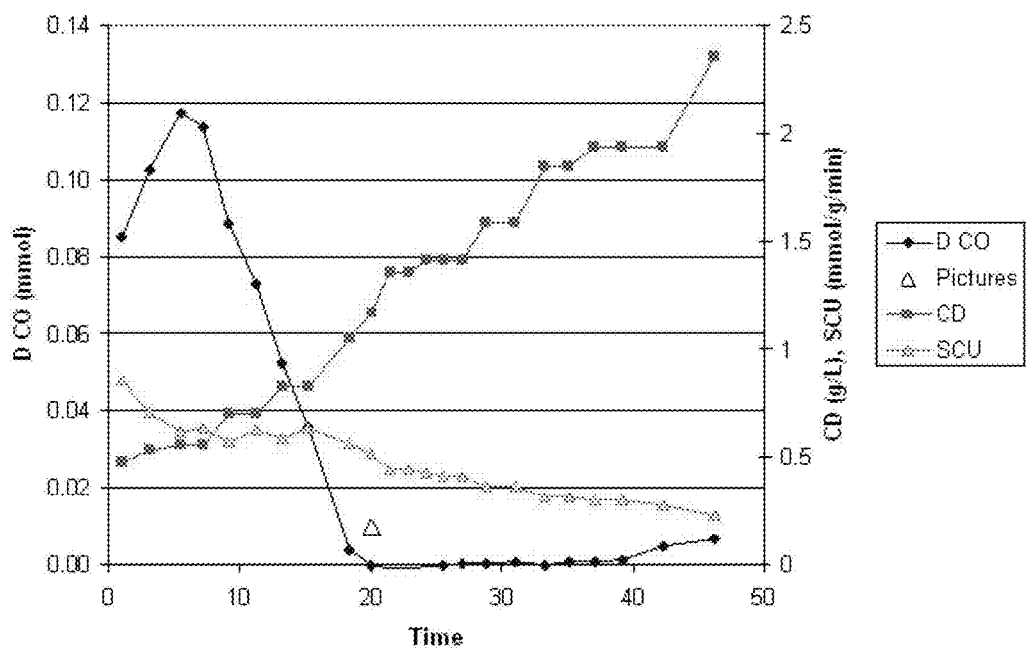
FIG. 6 illustrates growth of *Clostridium ljungdahlii* in 1× growth medium and a 50 ml/min syngas feed rate with a higher initial inoculum.

Bioreactor Run #6:

1× growth medium and 50 ml/min syngas feed rate was used in this experiment. This experiment was started with an inoculum of 4.8 g/L of bacteria. As shown in FIG. 6, after an initial lag period of about 10 hours, bacteria started to multiply at a doubling time of about 20 hours. Maximum calculated dissolved CO was about 0.12 mmol in the reactor broth.

Figure 7:
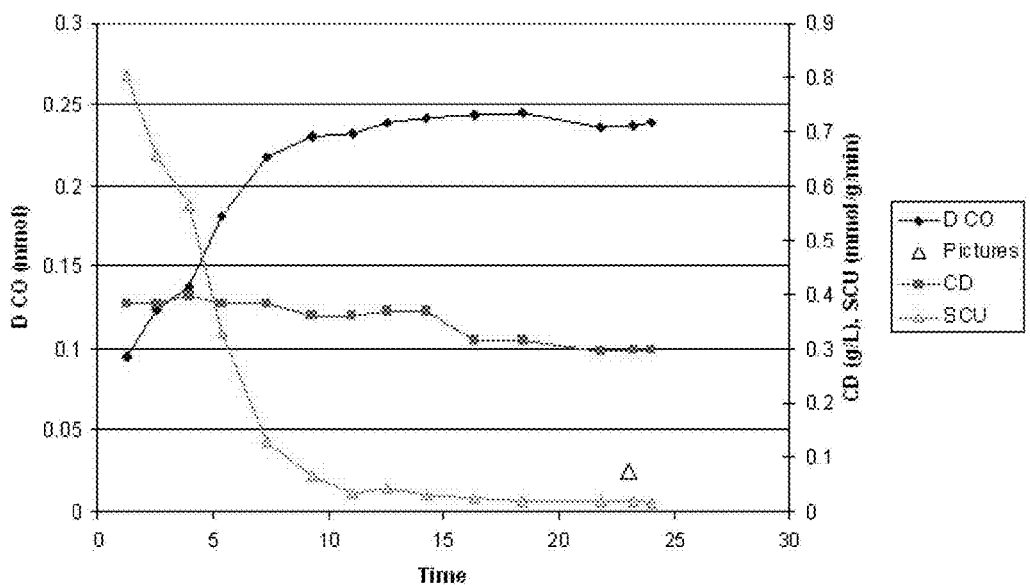
FIG. 7 illustrates growth of *Clostridium ljungdahlii* in 1.5× growth medium and a 45 ml/min syngas feed rate with a higher initial inoculum.

Bioreactor Run #7:

1.5× growth medium and 45 ml/min syngas feed rate was used in this experiment. This experiment was started with an inoculum of 3.8 g/L of bacteria. As shown in FIG. 7, bacterial cell density went down with time. Maximum calculated dissolved CO was about 0.25 mmol in the reactor broth.

Figure 8:
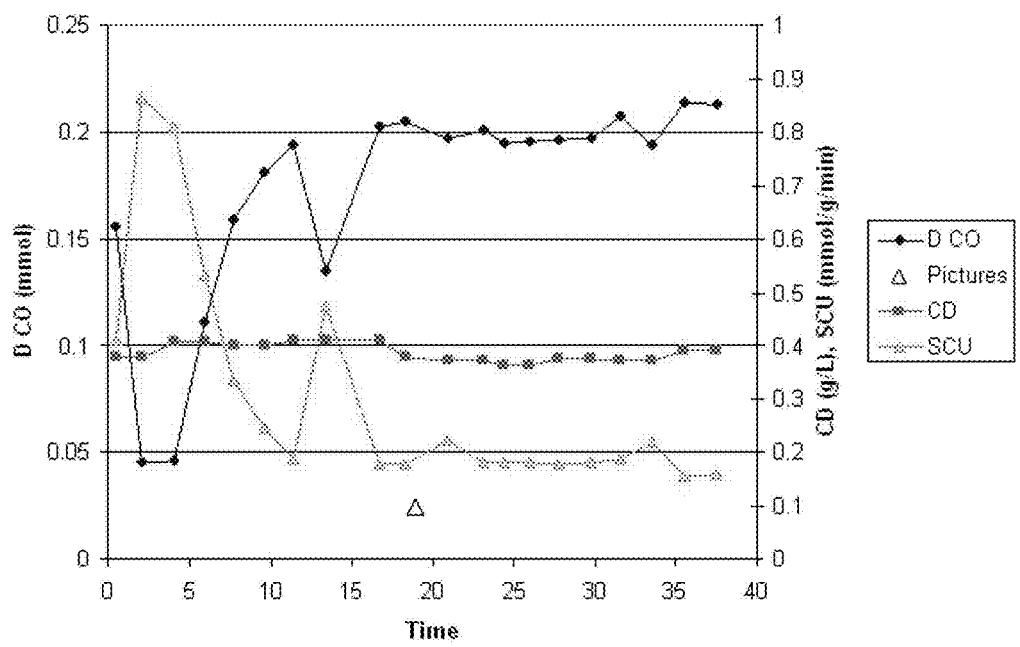
FIG. 8 illustrates growth of *Clostridium ljungdahlii* in 1.5× growth medium and a 35 ml/min syngas feed rate with a higher initial inoculum.

Bioreactor Run #8:

1.5× growth medium and 35 ml/min syngas feed rate was used in this experiment. This experiment was started with an inoculum of 3.8 g/L of bacteria. As shown in FIG. 8, bacterial cell density went down with time. Maximum calculated dissolved CO was about 0.22 mmol in the reactor broth.

Figure 9:
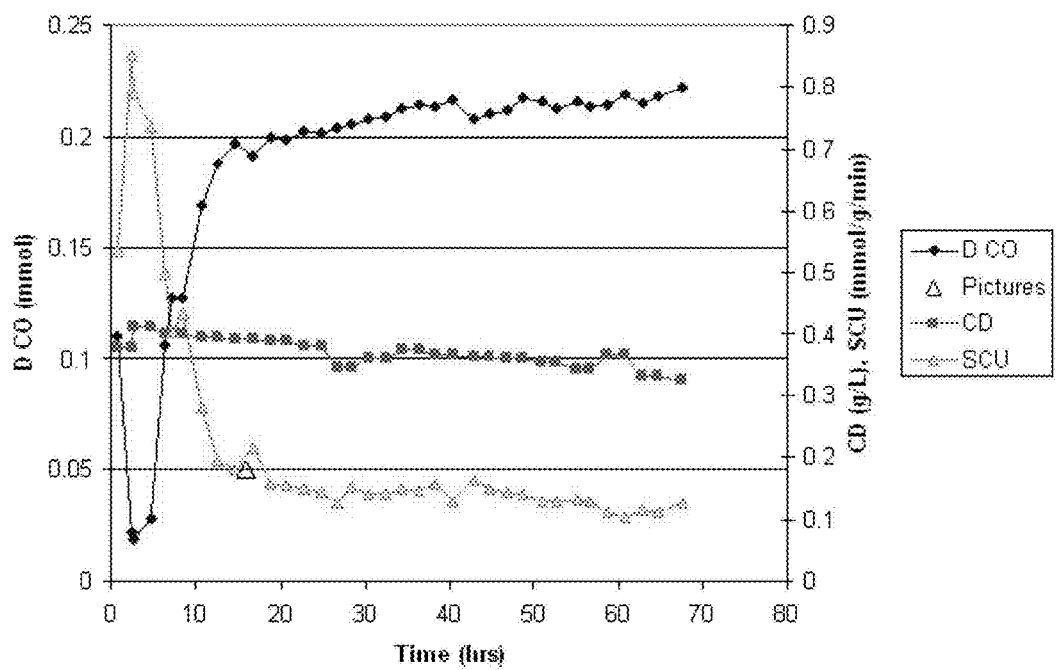
FIG. 9 illustrates growth of *Clostridium ljungdahlii* in 1.5× growth medium and a 30 ml/min syngas feed rate with a higher initial inoculum.

Bioreactor Run #9:

1.5× growth medium and 30 ml/min syngas feed rate was used in this experiment. This experiment was started with an inoculum of 3.8 g/L of bacteria. As shown in FIG. 9, bacterial cell density went down with time. Maximum calculated dissolved CO was around 0.22 mmol in the reactor broth.

Figure 10:
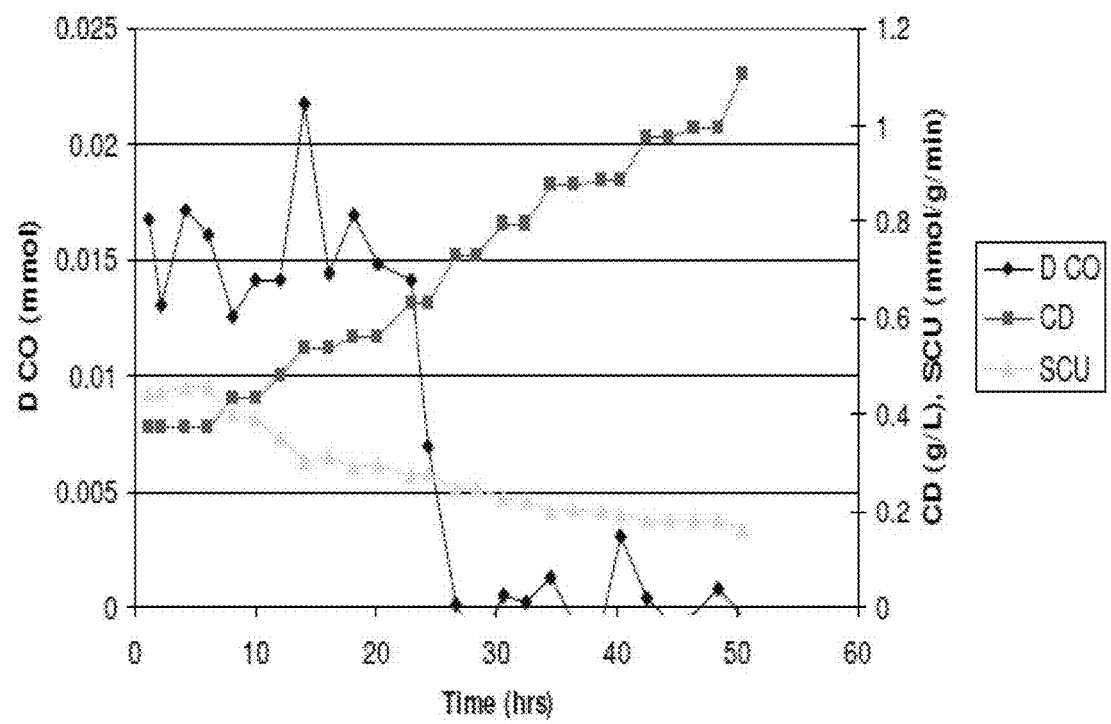
FIG. 10 illustrates growth of *Clostridium ljungdahlii* in 1.5× growth medium and a 20 ml/min syngas feed rate with a higher initial inoculum.

Bioreactor Run #10:

1.5× growth medium and 20 ml/min syngas feed rate was used in this experiment. This experiment was started with an inoculum of 3.8 g/L of bacteria. As shown in FIG. 10, bacterial cell density went up with time and achieved a doubling time of about 20 hours. Maximum calculated dissolved CO was around 0.22 mmol in the reactor broth.

Example 2: Growth on Alternative Nitrogen Sources

*Clostridium ljungdahlii* C-01 was grown in a bioreactor (BioFlo/CelliGen 115) with the following medium.

| Chemical | Target |
|---|---|
| $FeCl_2*4H_2O$ (g) | 0.24 |
| $H_3PO_4$ (ml) | 0.86 |
| KCl (g) | 3.00 |
| $MgCl_2*6H_2O$ (g) | 0.48 |
| $NH_4Cl$ (g) | 19.44 |
| Cysteine HCl (g) | 4.50 |
| 6x Med A2 (ml) | 15.0 |
| 6x TE (ml) | 4.6 |
| Water (L) | to 10 |

For each experiment, the $NH_4Cl$ was omitted from the medium and replaced with molar equivalents of one of the nitrogen containing compounds describes below.

| Chemical | Target (g) |
|---|---|
| l-Lysine | 26.57 |
| Ammonium acetate NH$_4$C$_2$H$_3$O$_2$ | 28.01 |
| Ammonium carbonate (NH$_4$)$_2$CO$_3$ | 17.46 |
| Ammonium bicarbonate (NH$_4$)HCO$_3$ | 28.73 |

The pH of these media was adjusted to ~4.0-4.4. Ammonium carbonate was also tested as base solution by using both 0.25M (24.02 g/L) and 0.125M (12.01 g/L) concentrations as substitute for 7.7% NaHCO$_3$.

Figure 11:
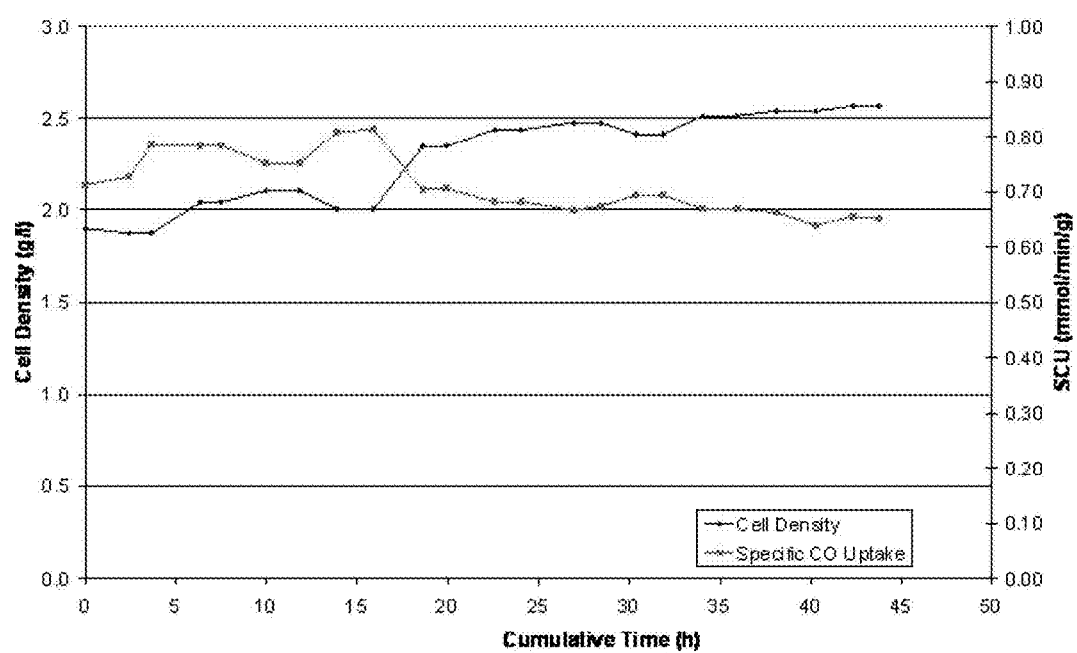
FIG. 11 shows specific carbon uptake of *Clostridium ljungdahlii* growing in medium containing ammonium chloride.

Specific carbon uptake of *Clostridium ljungdahlii* growing in medium containing ammonium chloride is shown in FIG. 11.

Figure 12:
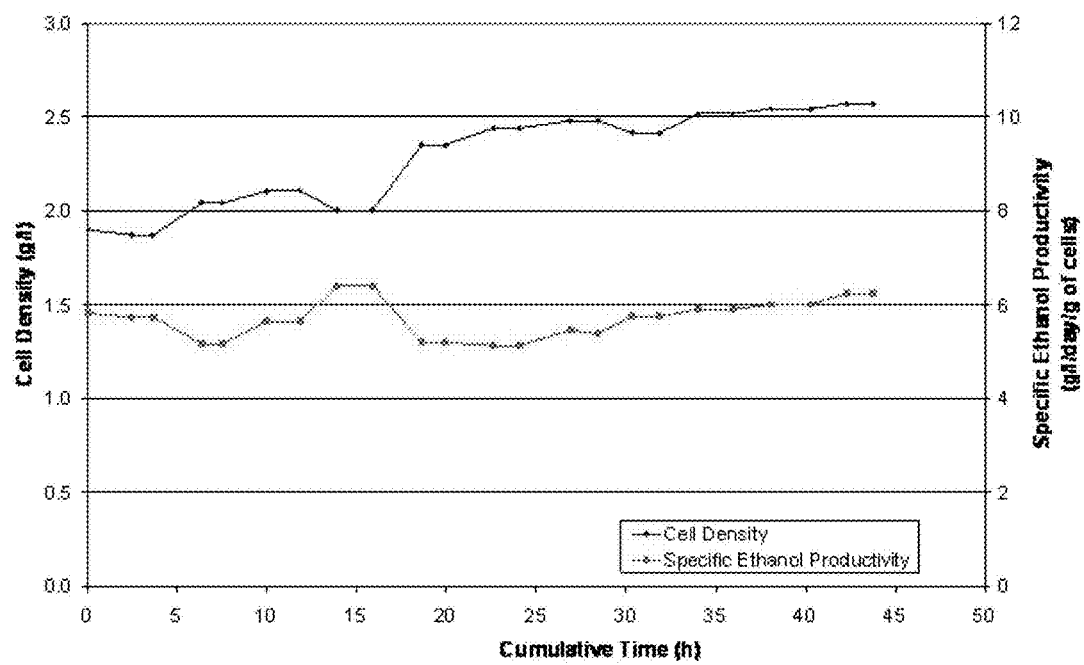
FIG. 12 shows specific ethanol productivity of *Clostridium ljungdahlii* growing in medium containing ammonium chloride.

Specific ethanol productivity of *Clostridium ljungdahlii* growing in medium containing ammonium chloride is shown in FIG. 12.

Figure 13:
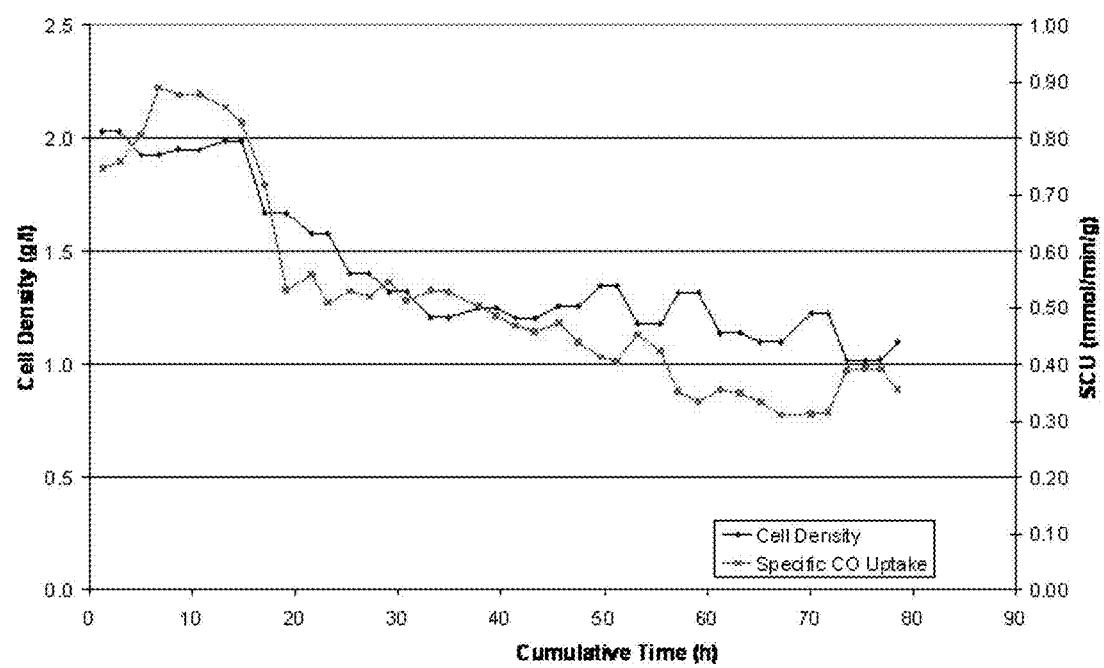
FIG. 13 illustrates specific carbon uptake of *Clostridium ljungdahlii* growing in medium containing 1-Lysine.

Specific carbon uptake of *Clostridium ljungdahlii* growing in medium containing l-Lysine is shown in FIG. 13.

Figure 14:
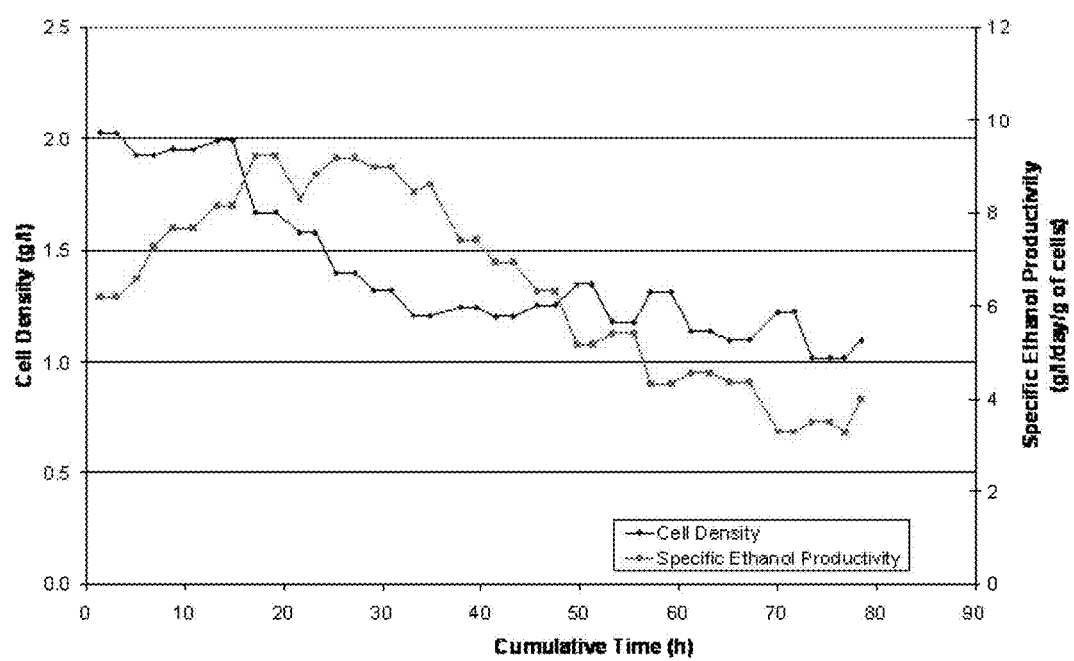
FIG. 14 illustrates specific ethanol productivity of *Clostridium ljungdahlii* growing in medium containing 1-Lysine.

Specific ethanol productivity of *Clostridium ljungdahlii* growing in medium containing l-Lysine is shown in FIG. 14.

Figure 15:
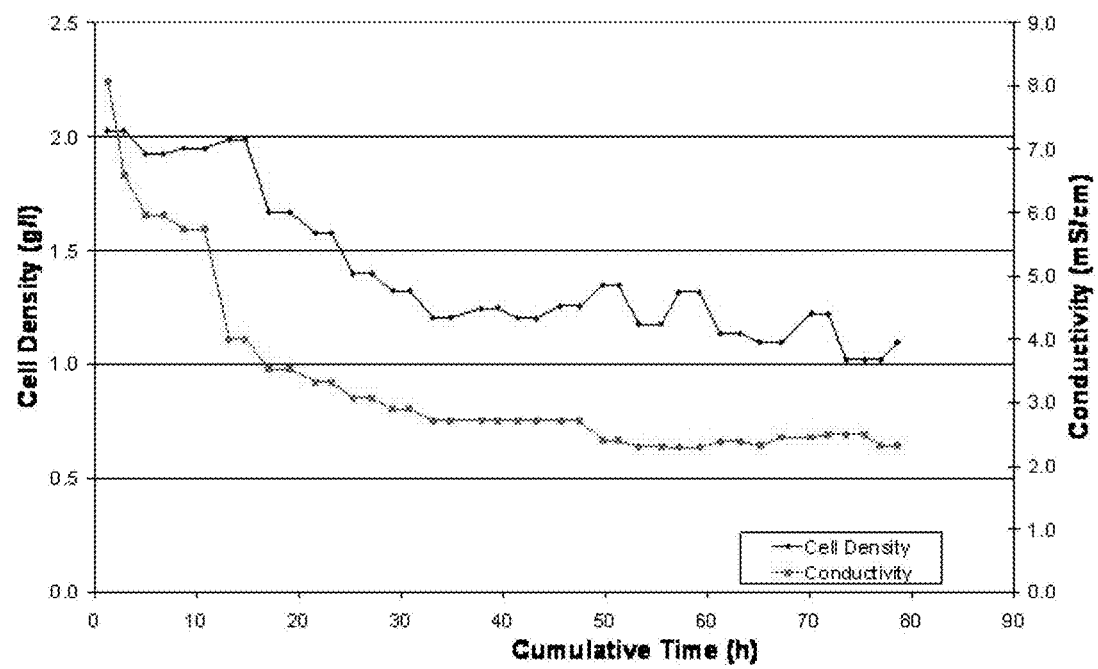
FIG. 15 shows conductivity of *Clostridium ljungdahlii* growing in medium containing 1-Lysine.

Conductivity of *Clostridium ljungdahlii* growing in medium containing l-Lysine is shown in FIG. 15.

Figure 16:
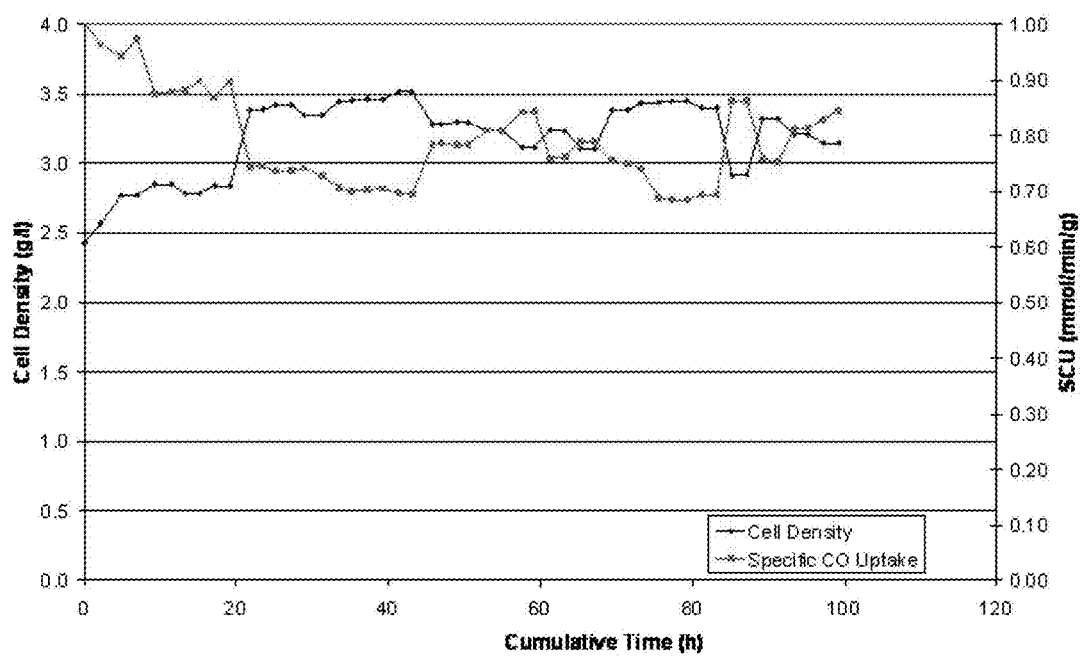
FIG. 16 shows specific carbon uptake of *Clostridium ljungdahlii* growing in medium containing ammonium acetate.

Specific carbon uptake of *Clostridium ljungdahlii* growing in medium containing ammonium acetate is shown in FIG. 16.

Figure 17:
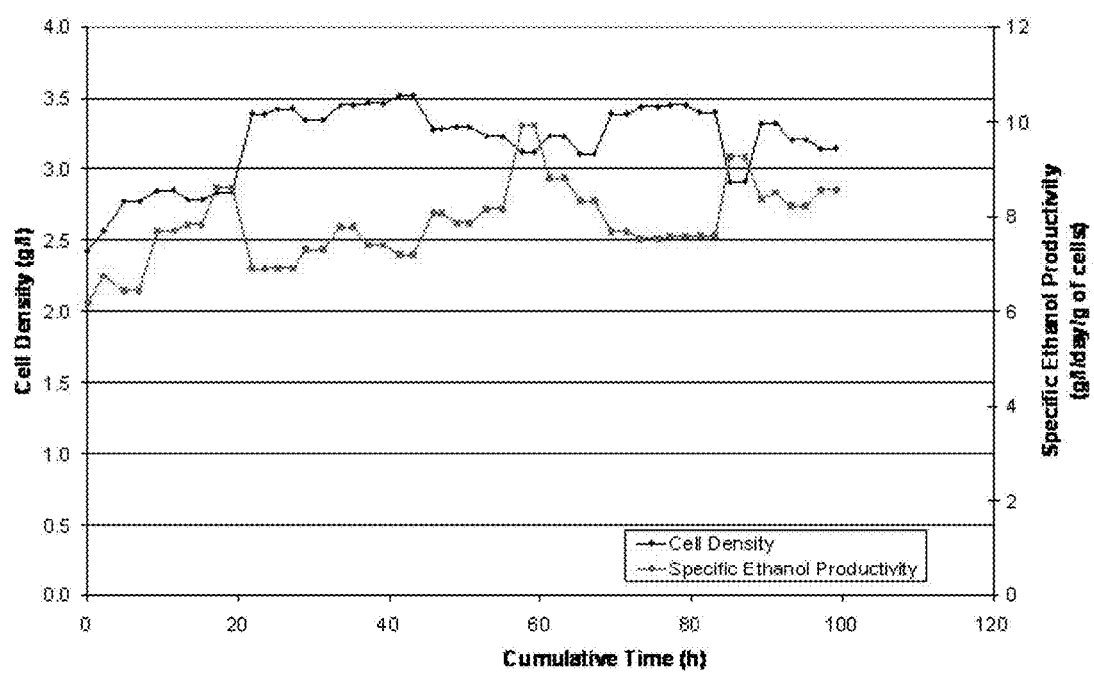
FIG. 17 illustrates specific ethanol productivity of *Clostridium ljungdahlii* growing in medium containing ammonium acetate.

Specific ethanol productivity of *Clostridium ljungdahlii* growing in medium containing ammonium acetate is shown in FIG. 17.

Figure 18:
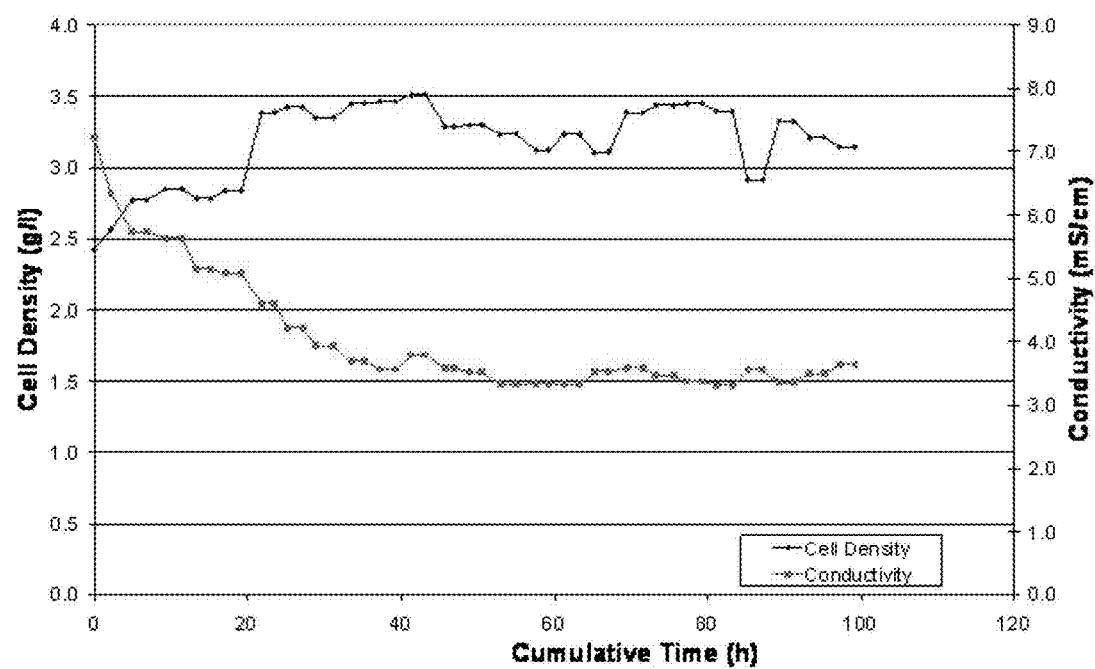
FIG. 18 illustrates conductivity of *Clostridium ljungdahlii* growing in medium containing ammonium acetate.

Conductivity of *Clostridium ljungdahlii* growing in medium containing ammonium acetate is shown in FIG. 18.

Figure 19:
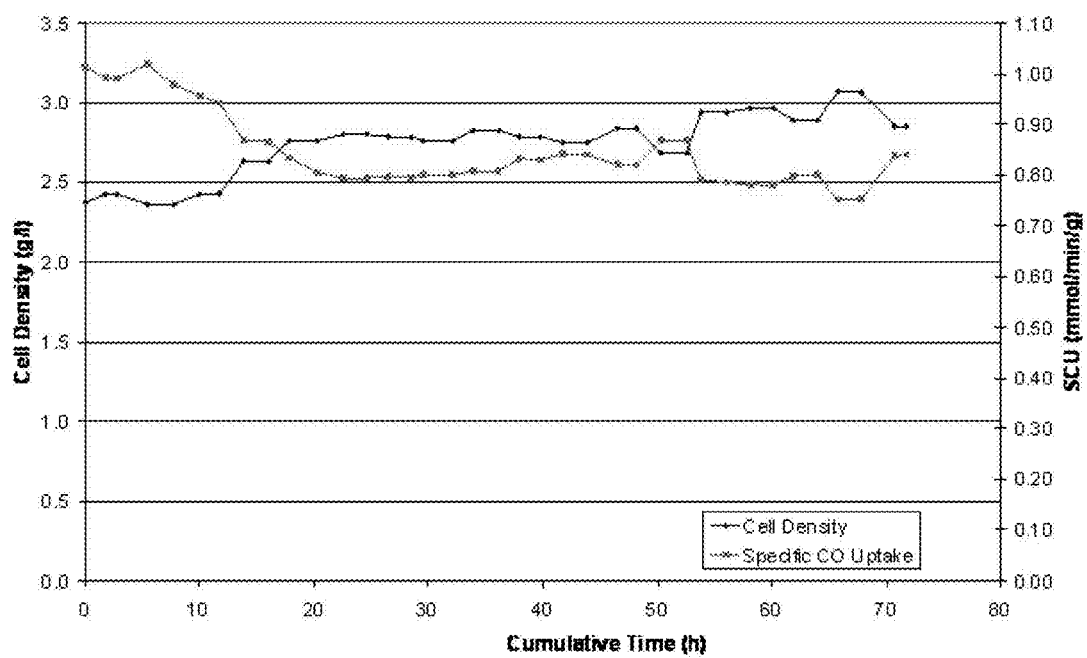
FIG. 19 shows specific carbon uptake of *Clostridium ljungdahlii* growing in medium containing ammonium carbonate.

Specific carbon uptake of *Clostridium ljungdahlii* growing in medium containing ammonium carbonate is shown in FIG. 19.

Figure 20:
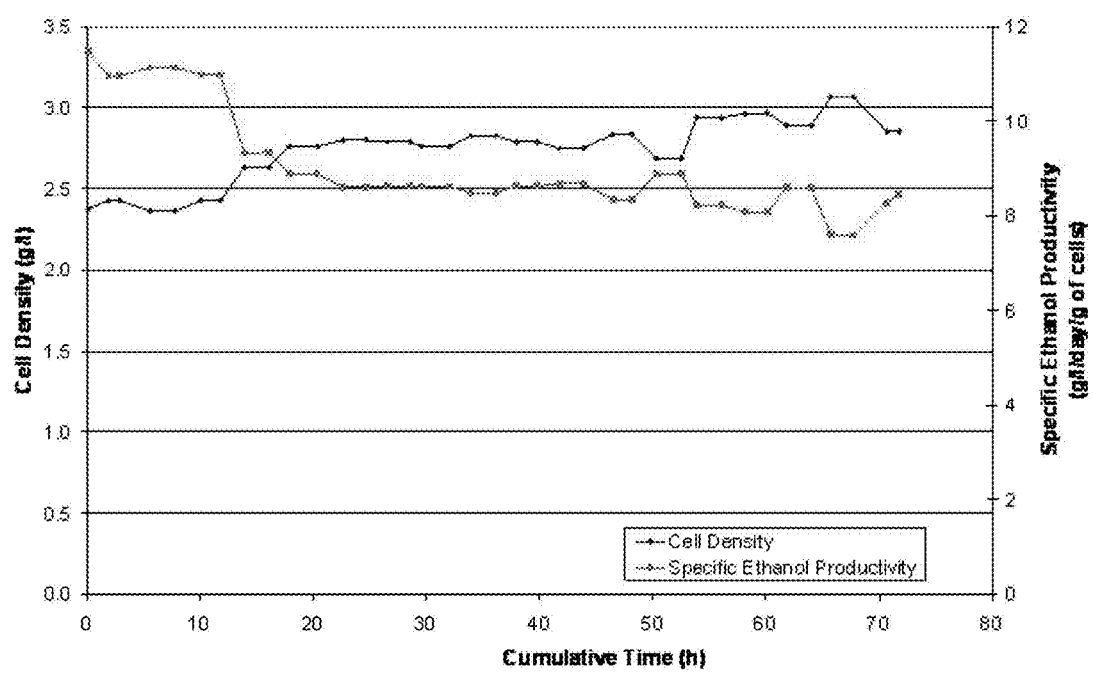
FIG. 20 shows specific ethanol productivity of *Clostridium ljungdahlii* growing in medium containing ammonium carbonate.

Specific ethanol productivity of CL growing in medium containing ammonium carbonate is shown in FIG. 20.

Figure 21:
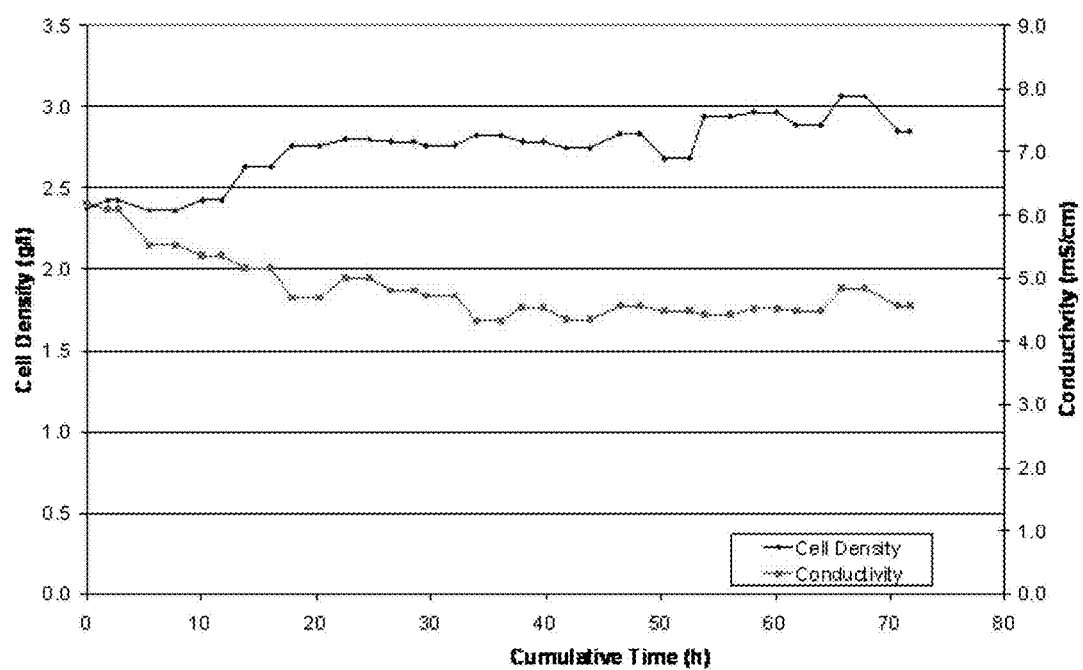
FIG. 21 illustrates conductivity of *Clostridium ljungdahlii* growing in medium containing ammonium carbonate.

Conductivity of *Clostridium ljungdahlii* growing in medium containing ammonium carbonate is shown in FIG. 21.

Figure 22:
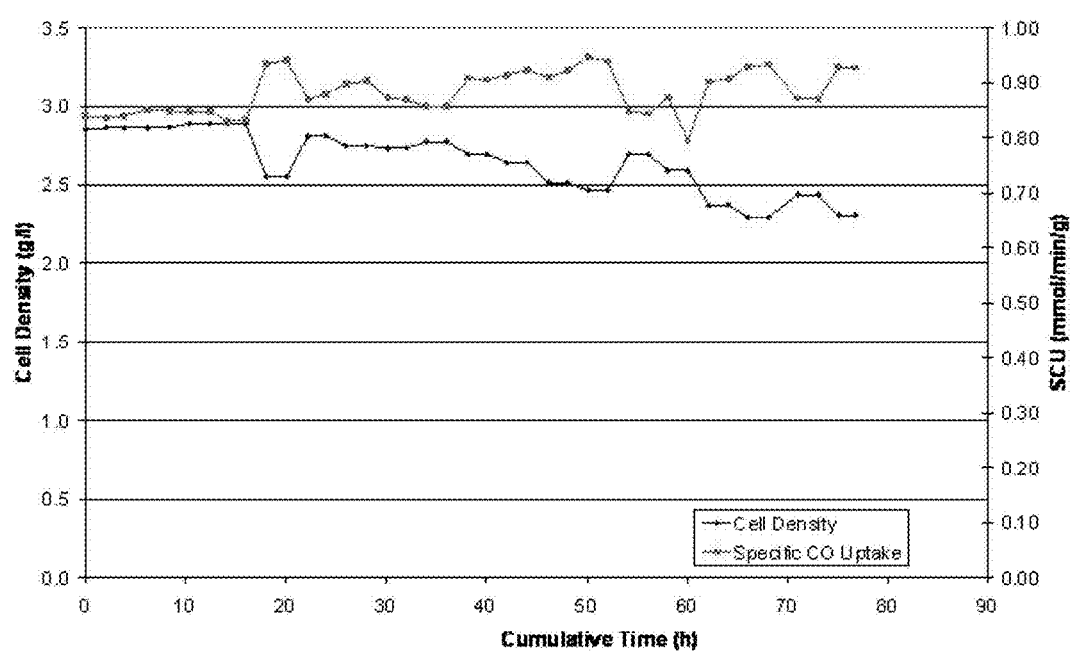
FIG. 22 illustrates specific carbon uptake of *Clostridium ljungdahlii* growing in medium with ammonium carbonate as base.

Specific carbon uptake of *Clostridium ljungdahlii* growing in medium with ammonium carbonate as base is shown in FIG. 22.

Figure 23:
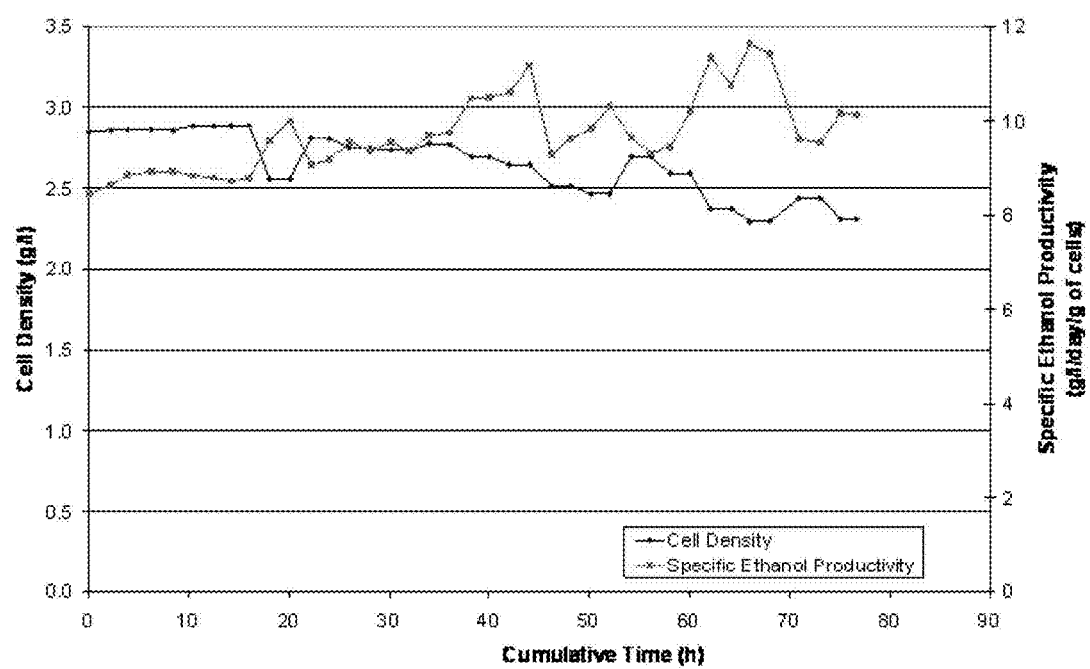
FIG. 23 shows specific ethanol productivity of *Clostridium ljungdahlii* growing in medium with ammonium carbonate as base.

Specific ethanol productivity of CL growing in medium with ammonium carbonate as base is shown in FIG. 23.

Figure 24:
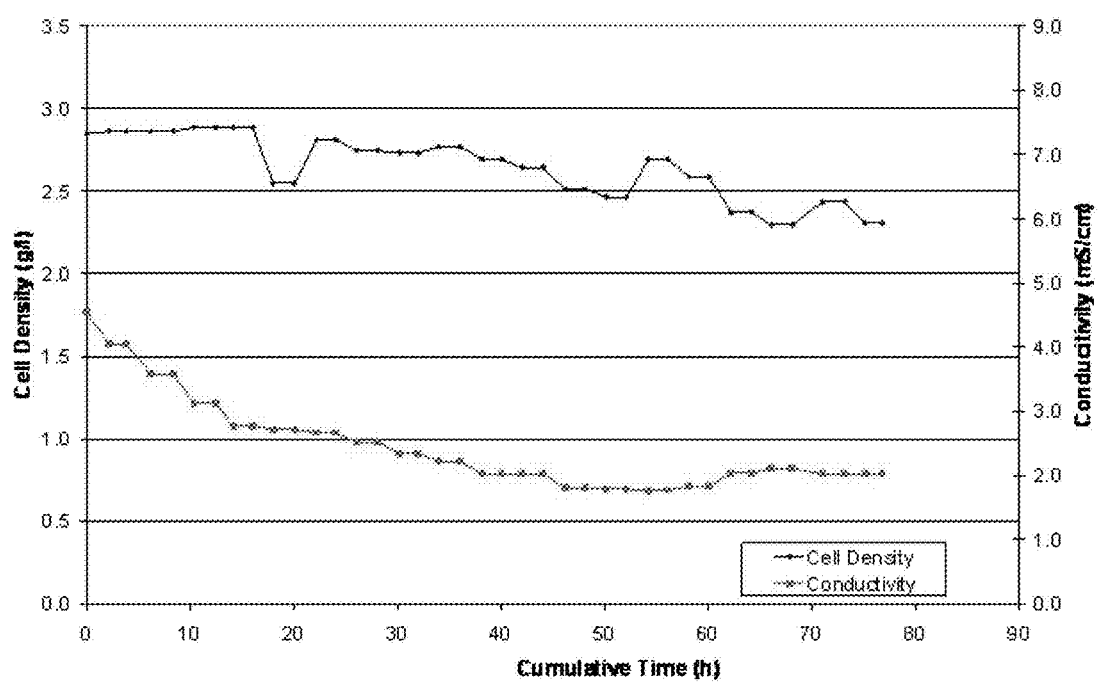
FIG. 24 shows conductivity of *Clostridium ljungdahlii* growing in medium with ammonium carbonate as base.

Conductivity of *Clostridium ljungdahlii* growing in medium with ammonium carbonate as base is shown in FIG. 24.

Specific carbon uptake of *Clostridium ljungdahlii* growing in medium with ammonium bicarbonate is shown in FIG. 25.

Specific ethanol productivity of *Clostridium ljungdahlii* growing in medium with ammonium bicarbonate is shown in FIG. 26.

Conductivity of *Clostridium ljungdahlii* growing in medium with ammonium bicarbonate is shown in FIG. 27.

The following Tables summarize the results.

| Specific Carbon Uptake and Specific Ethanol Productivity | | | |
|---|---|---|---|
| Treatment | SCU Average | SCU SD | Sp. EtOH Productivity Average |
| Baseline | 0.711 | 0.054 | 5.706 |
| l-Lysine (medium) | 0.521 | 0.179 | 6.421 |
| Ammonium acetate (medium) | 0.792 | 0.082 | 7.862 |
| Ammonium carbonate (medium) | 0.846 | 0.075 | 9.009 |
| Ammonium carbonate (base) Total | 0.883 | 0.039 | 9.718 |
| 0.25M | 0.867 | 0.034 | 9.091 |
| 0.125M | 0.894 | 0.038 | 10.165 |
| Ammonium bicarbonate (medium) | 0.848 | 0.047 | 8.726 |

| Conductivity of Fermentor Medium (mS/cm) | | |
|---|---|---|
| Treatment | Conductivity Raw Decrease* | Conductivity Average |
| l-Lysine (medium) | -5.77 | 3.291 |
| Ammonium acetate (medium) | -4.75 | 4.027 |
| Ammonium carbonate (medium) | -3.74 | 4.839 |
| Ammonium carbonate (base) Total | -6.30 | 2.445 |
| 0.25M | -5.73 | 3.065 |
| 0.125M | -6.30 | 1.982 |
| Ammonium bicarbonate (medium) | -4.05** | 4.300 |

*Uses the initial value from the Lysine experiment (8.07 mS/cm) as the baseline value.
**Omits outlying measurements near beginning of experiment.

| Ammonium Ion Concentration | |
|---|---|
| Treatment | Ammonium Ion Concentration (ppm) Average |
| Baseline | 145.71 |
| Ammonium carbonate (0.25M base) | 235.26 |
| Ammonium carbonate (0.125M base) | 220.11 |
| Ammonium bicarbonate (medium) | 184.41 |

Results indicate that nitrogenous compounds, especially those containing ammonium ions, can be used as substitutes for ammonium chloride. L-Lysine used in medium was not successful as a nitrogen source to obtain high performance. Lysine use led to initial gains in both specific carbon uptake (SCU) and specific ethanol productivity (SEP), but ultimately led to marked decreases in both of those metrics. The raw value for SCU was decreased by 58%, while the raw value for SEP was decreased by 47%. Average SCU was decreased by 26%, a significant change. Average SEP was increased by 12%, but that increase was not statistically significant due to a very large standard deviation. Cell density decreased over the course of the experiment from 2.03 g/l to 1.02 g/l. Conductivity raw value decreased 71%, from 8.07 mS/cm to 2.30 mS/cm, with an average over the time course of the experiment of 3.291 mS/cm. The majority of the time in this experiment, conductivity was less than 3.0 mS/cm.

Ammonium acetate as nitrogen source in medium led to a slight increase of only 11% in average SCU, a value which is not statistically significant. However, the raw value for SCU decreased from the beginning to the end of the experiment (0.943 vs. 0.830), a 12% drop. There was a significant increase of 37% in average SEP when compared to baseline averages. The raw value for SEP increased during the experiment from 6.43 to 8.57, an increase of 25%. Conductivity during this experiment decreased by 58%, to a low of 3.32 mS/cm (using the initial value from the lysine experiment as a baseline for conductivity in PP-A1 medium), with an average value of 4.027 mS/cm. For the majority of the experiment the conductivity value was less than 4.0.

When ammonium carbonate was used in the medium as a nitrogen source, significant increases in both SCU and SEP were observed. SCU increased by 19% and SEP increased by 57%. The raw values for SCU and SEP decreased during the experiment by 15% and 23%, respectively. Conductivity during this experiment decreased by 46%, to a low of 4.33 mS/cm, with an average value of 4.839 mS/cm.

Ammonium carbonate was also tested as nitrogen source by omitting the compound from the medium recipe and instead using it as the base solution. This method of supplying ammonium carbonate resulted in overall significant increases in SCU (19%) and SEP (41%) versus baseline. Two different concentrations of ammonium carbonate were used, 0.25M and 0.125M, and there were slightly different results for each. Each concentration yielded significantly higher SCU and SEP than the reactor baseline. Each base concentration resulted in slightly different values for the two measured metrics, but the standard deviations of these measurements overlap each other. The conductivity was decreased by the two base solutions by 71% (0.25M) and 78% (0.125M) to respective lows of 2.34 mS/cm and 1.77 mS/cm. The averages were 3.065 mS/cm and 1.982 mS/cm, respectively. The concentration of the ammonium ion in the reactor was measured just before and throughout the duration of the ammonium carbonate as base experiment. The results of these measurements show that the reactor was supplied with excess ammonium ion (50-62%) during the experiment.

Ammonium bicarbonate was also tested as an additive to the medium. The experimental data show that there were significant increases in both SCU and SEP. Average SCU was increased above the baseline by 19% and average SEP was increased above baseline by 53%. Conductivity during this experiment decreased by 50%, to a low of 4.02 mS/cm, with an average value of 4.3 mS/cm. Ammonium ion concentration was also monitored during this phase of the experiment. The values show that the ion was in excess by 26% in the reactor.

Example 3: Effects of Step-Wise Increases in Osmolarity on Culture Performance

*Clostridium ljungdahlii* C-01 was grown in a bioreactor (BioFlo/CelliGen 115) with the following medium. The average media flow per gram of cells was 1 mL/g/minute.

| Chemical | Target |
| --- | --- |
| $FeCl_2 \cdot 4H_2O$ (g) | 0.24 |
| $H_3PO_4$ (ml) | 0.86 |
| KCl (g) | 3.00 |
| $MgCl_2 \cdot 6H_2O$ (g) | 0.48 |
| $NH_4Cl$ (g) | 19.44 |
| Cysteine HCl (g) | 4.50 |
| 6x Med A2 (ml) | 15.0 |
| 6x TE (ml) | 4.6 |
| Water (L) | to 10 |

In this 21 day experiment the conductivity of the culture broth was increased using NaCl. Each addition of NaCl at given intervals are shown in FIG. 28 according to the following schedule.

| NaCl concentratons after each addition. | |
| --- | --- |
| Time (hrs) | Concentration (g/L) |
| 163 | 1 |
| 307 | 2 |
| 422 | 3 |
| 498 | 4 |
| 597 | 5.23 |
| 618 | 5 |
| 646 | 6 |
| 720 | 7 |
| 793 | 8 |
| 883 | 9 |
| 935 | 10 |
| 1001 | 11 |
| 1057 | 12 |
| 1119 | 13 |

The conductivity of the culture rose with each addition of NaCl. Specific Carbon Uptake (SCU), an indicator of culture activity was measured through out the experiment. FIG. 28 shows that with each NaCl addition the SCU was diminished for a period of time but would recover after a short adaptation period.

FIG. 28 can be divided into three areas of interest; 0-500 hrs (1), 500-1100 hrs (2), and 1100-1200 hrs. Area 1, where the conductivity was less than 15 mS/cm, shows addition of NaCl has less impact on the SCU: only small losses of SCU followed by full recoveries. Area 2, where the conductivity is above 15 mS/cm, shows addition of NaCl has a higher impact on the SCU: large swings of SCU. In this area the NaCl additions caused large drops in SCU followed by large up-swings. In the final area when the conductivity rose to about 30 mS/cm or higher culture lost its activity.

Example 4: Effects of Rapid Increases in Osmolarity on Culture Performance

*Clostridium ljungdahlii* C-01 was grown in a bioreactor (BioFlo/CelliGen 115) with the same medium as described in Example 3. The average media flow per gram of cells was 1.1 mL/g/minute.

In this 10 day experiment, NaCl concentration in the broth was increased twice as fast the rate of increase of NaCl concentration in Example 3 according to the following schedule.

NaCl concentratons after each addition.

| Time (hrs) | Concentration (g/L) |
|---|---|
| 96 | 7 |
| 121 | 9 |
| 144 | 11 |
| 498 | 13 |

FIG. 29 shows SCU of the culture at different conductivities. As in the Example 3 culture lost its activity once the conductivity of the culture reach around 30 mS/cm.

Example 5: Effect of CO Feed Rate on Conductivity

*Clostridium ljungdahlii* C-01 was grown in a bioreactor (BioFlo/CelliGen 115) with the same medium as described in Example 3.

Conductivity of the culture was adjusted by adjusting the strength of the growth medium, for example concentration of all the components, except vitamin in the growth medium was increased by 1.5 and 2 times to increase the conductivity of the culture from ~7 mS to ~9.5 mS and ~12 mS respectively.

Experiments were started with the initial cell density of 0.38 (+/−0.02) or 0.785 g/l. Syngas composition was 30% CO, 15% $H_2$, $CO_2$ 10% and 45% $N_2$. Several start-up experiments were done at each given culture conductivity to determine the appropriate (that can be practically used) specific gas feed rate for given culture conductivity. Through these experiments the appropriate gas feed rate was determined for a given culture conductivity. As illustrated in FIG. 30, the appropriate/functional CO feed rate was plotted against culture conductivity, where $y=-6.0327x+12.901$ Specific CO feed rate=molar amounts of CO per gram of cells Appropriate/functional CO feed rate=the CO feed rate that C-01 can double within 40 hours.

While the invention herein disclosed has been described by means of specific embodiments, examples and applications thereof, numerous modifications and variations could be made thereto by those skilled in the art without departing from the scope of the invention set forth in the claims.

What is claimed is:

1. A process for fermenting a CO-containing gaseous substrate to produce ethanol comprising:
   (a) providing a CO-containing gaseous substrate to a fermentation medium;
   (b) contacting the resultant CO-containing fermentation medium of step (a) with one or more acetogenic bacteria to form a mixture;
   (c) fermenting the mixture of step (b);
   (d) measuring the specific feed rate of the CO-containing gaseous substrate and the conductivity of the mixture of step c);
   (e) providing the CO-containing gaseous substrate to the mixture to maintain a conductivity (y) to specific gas feed rate (x) of the CO-containing gaseous substrate according to a formula where y=−6.0327x+12.901 where the conductivity is about 30 mS/cm or less, until reaching a target cell density of the one or more acetogenic bacteria, wherein x is about 0.2 to about 07 mmole/minute/gram of cells of the acetogenic bacteria;
   maintaining a cell density of the one or more acetogenic bacteria above a target cell density; and
   obtaining ethanol;
   wherein the process is effective for maintaining a space time yield (STY) of about 10 g ethanol/(L-day) or more.

2. The process of claim 1 wherein the target cell density is about 3 to about 30 g/L.

3. The process of claim 1 wherein the process is effective for maintaining an $H_2$ conversion of about 25% or more.

4. The process of claim 1 wherein the process is effective for maintaining a CO uptake in a range of about 0.001 to about 10 mmole/minute/gram of dry cells of the one or more acetogenic bacteria.

5. The fermentation process of claim 1 wherein the CO containing, gaseous substrate has a $CO/CO_2$ ratio of about 0.75 or more.

6. The fermentation process of claim 1 wherein the one or more acetogenic bacteria is selected from the group consisting of *Acetogenium kivui, Acetoanaerobium noterae, Acetobacterium woodii, Blautia producta, Butyribacterium methylotmphicum, Caldanaerobacter subterraneous, Caldanaerobaeter subterraneous pacificus, Carboxydothermus hydrogenoformans, Clostridium aceticum, Clostridium acetobutylicum, Clostridium autoethanogenum, Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* Pit (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus* and *Thermoamerobacter kivui*.

* * * * *